United States Patent
Inada et al.

(10) Patent No.: US 10,228,365 B2
(45) Date of Patent: Mar. 12, 2019

(54) METHOD FOR MEASURING CARBOHYDRATE METABOLISM ABILITY, AND COMPOSITION FOR USE IN SAID METHOD

(71) Applicant: OTSUKA PHARMACEUTICAL CO., LTD., Tokyo (JP)

(72) Inventors: Makoto Inada, Osaka (JP); Jun-ichi Kunizaki, Osaka (JP); Kazuki Tobita, Osaka (JP); Suguru Akamatsu, Osaka (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 14/423,021

(22) PCT Filed: Aug. 20, 2013

(86) PCT No.: PCT/JP2013/072204
§ 371 (c)(1),
(2) Date: Feb. 20, 2015

(87) PCT Pub. No.: WO2014/030650
PCT Pub. Date: Feb. 27, 2014

(65) Prior Publication Data
US 2015/0204852 A1    Jul. 23, 2015

(30) Foreign Application Priority Data
Aug. 20, 2012   (JP) ................. 2012-181922

(51) Int. Cl.
*G01N 33/497*   (2006.01)
*G01N 33/50*    (2006.01)
*G01N 33/58*    (2006.01)
*G01N 33/60*    (2006.01)
*G01N 33/66*    (2006.01)
*A61B 5/083*    (2006.01)
*A61K 49/00*    (2006.01)
*A61B 5/08*     (2006.01)
*A61B 5/00*     (2006.01)
*G06F 19/00*    (2018.01)

(52) U.S. Cl.
CPC ....... *G01N 33/5038* (2013.01); *A61B 5/0813* (2013.01); *A61B 5/0836* (2013.01); *A61B 5/7275* (2013.01); *A61K 49/0004* (2013.01); *G01N 33/497* (2013.01); *G01N 33/5088* (2013.01); *G06F 19/00* (2013.01); *G01N 33/60* (2013.01); *G01N 33/66* (2013.01); *G01N 2400/00* (2013.01); *G01N 2800/042* (2013.01); *G01N 2800/52* (2013.01); *G01N 2800/56* (2013.01); *Y10T 436/144444* (2015.01); *Y10T 436/204998* (2015.01)

(58) Field of Classification Search
CPC ... A61B 5/0813; A61B 5/0836; A61B 5/7275; A61K 49/0004; G01N 2400/00; G01N 2800/042; G01N 2800/52; G01N 2800/56; G01N 33/497; G01N 33/5038; G01N 33/5088; G01N 33/66; G01N 33/60; Y10T 436/204998; Y10T 436/10; Y10T 436/104998; Y10T 436/13; Y10T 436/144444
USPC ............... 436/8, 14, 56, 57, 95, 133; 435/14
See application file for complete search history.

(56) References Cited

U.S. PATENT DOCUMENTS

| | | | |
|---|---|---|---|
| 4,328,229 A | 5/1982 | Fujii et al. | |
| 4,451,260 A | 5/1984 | Mitra | |
| 4,790,327 A | 12/1988 | Despotis | |
| 4,830,010 A | 5/1989 | Marshall | |
| 5,233,997 A | 8/1993 | Klein et al. | |
| 5,670,331 A | 9/1997 | Kouni et al. | |
| 5,707,602 A | 1/1998 | Klein | |
| 5,916,538 A * | 6/1999 | Kohno | A61K 49/00 424/9.1 |
| 5,944,670 A | 8/1999 | Katzman | |
| 6,113,875 A | 9/2000 | Nystrom et al. | |
| 6,186,958 B1 | 2/2001 | Katzman et al. | |
| 6,232,448 B1 | 5/2001 | Yoshikubo et al. | |
| 6,294,151 B1 | 9/2001 | Hayakawa et al. | |
| 6,355,416 B1 | 3/2002 | Abramson | |
| 6,432,382 B1 | 8/2002 | Mehta | |
| 6,509,002 B1 | 1/2003 | Kohno et al. | |
| 6,616,941 B1 | 9/2003 | Seo et al. | |
| 6,740,305 B1 | 5/2004 | Ajami | |
| 6,797,256 B2 | 9/2004 | Inada et al. | |
| 7,018,613 B2 | 3/2006 | Nakagawa et al. | |
| 8,883,121 B2 | 11/2014 | Inoue et al. | |

(Continued)

FOREIGN PATENT DOCUMENTS

| EP | 0 411 629 A2 | 2/1991 |
|---|---|---|
| EP | 0 860 170 A1 | 8/1998 |

(Continued)

OTHER PUBLICATIONS

Singal et al. Diabetes Technology & Therapeutics, vol. 12, No. 12, 2010, pp. 947-953.*

(Continued)

*Primary Examiner* — Maureen Wallenhorst
(74) *Attorney, Agent, or Firm* — Finnegan, Henderson, Farabow, Garrett & Dunner, LLP

(57) ABSTRACT

A method is provided for measuring and evaluating rapidly and with high accuracy a subject's glucose metabolism. The method uses a labeled C-breath test and a composition that is suitably used in the method. The composition contains as active ingredient glucose labeled with at least one isotope of C, wherein the glucose is converted in the subject to labeled carbon dioxide that is excreted in expired air. This method also allows for the determination of a stage of a patient in whom diabetes has developed as well as for a stage before the onset of diabetes, and monitors the state (diabetes condition including a state before onset of diabetes) over time.

7 Claims, 11 Drawing Sheets

(56) References Cited

U.S. PATENT DOCUMENTS

| | | |
|---|---|---|
| 2001/0010825 A1 | 8/2001 | Shimizu et al. |
| 2001/0021499 A1 | 9/2001 | Wielburski et al. |
| 2002/0132283 A1 | 9/2002 | Inada et al. |
| 2002/0187985 A1 | 12/2002 | Cincotta |
| 2003/0068272 A1 | 4/2003 | Inada et al. |
| 2003/0129131 A1 | 7/2003 | Inada et al. |
| 2003/0190283 A1 | 10/2003 | Nakagawa et al. |
| 2003/0215500 A1 | 11/2003 | Ohta et al. |
| 2004/0213763 A1 | 10/2004 | Friedman et al. |
| 2004/0234452 A1 | 11/2004 | Inada et al. |
| 2005/0147560 A1 | 7/2005 | Yatscoff et al. |
| 2006/0020440 A1 | 1/2006 | Hellerstein |
| 2006/0263296 A1 | 11/2006 | Kinniburgh et al. |
| 2006/0280681 A1 | 12/2006 | Harano |
| 2006/0280682 A1 | 12/2006 | Hellerstein |
| 2007/0248540 A1 | 10/2007 | Hellerstein |
| 2008/0233048 A1 | 9/2008 | Inoue et al. |
| 2009/0131810 A1 | 5/2009 | Oren et al. |
| 2010/0041082 A1 | 2/2010 | Hellerstein |
| 2010/0055799 A1 | 3/2010 | Inada et al. |
| 2010/0209385 A1 | 8/2010 | Febbraio et al. |
| 2011/0166792 A1 | 7/2011 | Takahata |
| 2012/0003335 A1 | 1/2012 | Xie et al. |
| 2012/0100073 A1 | 4/2012 | Mach et al. |
| 2013/0143253 A1 | 6/2013 | Inada et al. |
| 2014/0087407 A1 | 3/2014 | Deutz et al. |
| 2014/0135359 A1 | 5/2014 | Martineau |
| 2014/0329274 A1 | 11/2014 | Bowen et al. |
| 2015/0017100 A1 | 1/2015 | Inoue et al. |
| 2015/0031068 A1 | 1/2015 | Glick et al. |
| 2015/0204852 A1 | 7/2015 | Inada et al. |

FOREIGN PATENT DOCUMENTS

| | | |
|---|---|---|
| EP | 1285668 A1 | 2/2003 |
| EP | 1 374 911 A1 | 1/2004 |
| JP | 46-26989 B1 | 8/1971 |
| JP | 64-61467 | 3/1989 |
| JP | 02-172918 A | 7/1990 |
| JP | 03-66613 A | 3/1991 |
| JP | 07-300430 | 11/1995 |
| JP | 10-500995 A | 1/1998 |
| JP | 10-67689 | 3/1998 |
| JP | 11-124343 | 5/1999 |
| JP | 2000-507802 | 6/2000 |
| JP | 2002-513911 | 5/2002 |
| JP | 2008-292506 | 12/2006 |
| JP | 2008-543787 | 12/2006 |
| JP | 4007-00653 B2 | 11/2007 |
| JP | 2008-44889 A | 2/2008 |
| JP | 2008-531068 A | 8/2008 |
| JP | 2008-538275 A | 10/2008 |
| JP | 2008-292506 | 12/2008 |
| JP | 2009-515139 A | 4/2009 |
| JP | 2010-502194 A | 1/2010 |
| JP | 2010-44093 | 2/2010 |
| JP | 2011-106846 A | 6/2011 |
| JP | 2011-141273 | 7/2011 |
| KR | 20010017804 | 3/2001 |
| WO | WO 91/18105 A1 | 11/1991 |
| WO | WO 96/14091 | 5/1996 |
| WO | WO 96/36330 | 11/1996 |
| WO | WO 97/02050 | 1/1997 |
| WO | WO 97/35622 | 10/1997 |
| WO | WO 97/40856 | 11/1997 |
| WO | WO 98/09658 | 3/1998 |
| WO | WO 99/56790 | 11/1999 |
| WO | WO 00/61197 | 10/2000 |
| WO | WO 02/072153 | 9/2002 |
| WO | WO 2004/87146 | 10/2004 |
| WO | WO 2006/090880 | 8/2006 |
| WO | WO 2006/112513 | 10/2006 |
| WO | WO 2006/135879 | 12/2006 |
| WO | WO 2007/007100 | 1/2007 |
| WO | WO 2007/013409 | 2/2007 |
| WO | WO 2008/028116 | 3/2008 |
| WO | WO 2008/138993 | 11/2008 |
| WO | WO 01/82979 | 8/2011 |

OTHER PUBLICATIONS

Matsubayashi et al.; "$^{13}$C-Breath Test Data Analysis Method", pp. 102-110, 2002.
Kagaku no Ryoiki; "Application of Stable Isotopes in Medicine, Pharmacy, and Biology", Journal of Japanese Chemistry, pp. 149-163, (1975).
Kajiwara; "Radioisotopes", 41, pp. 47-50, (1992).
International Search Report from the Japanese Patent Office for International Application No. PCT/JP2013/072204, dated Sep. 24, 2013.
Dillon, E. Lichar, "Novel Noninvasive Breath Test Method for Screening Individuals at Risk for Diabetes," Diabetes Care, 32:430-435 (2009).
Extended European Search Report for corresponding EP Application No. 13831608.8 dated Mar. 30, 2016.
Tsuchiya, Masako et al., "Evaluation of a novel non-invasive $^{13}$C-glucose breath test for the identification of diabetes mellitus in cirrhotic patients," Hepatology Research, vol. 42, No. 12, pp. 1196-1201 (2012).
Blaak et al. Weight Reduction and the Impaired Plasma-Derived Free Fatty Acid Oxidation in Type 2 Diabetic Subjects, The Journal of Clinical Endocrinology & Metabolism 2001, vol. 86. No. 4, pp. 1638-1644.
Braden, Barbara et al., "The [$^{13}$C]Acetate Breath Test Accurately Reflects Gastric Emptying of Liquids in Both Liquid and Semisolid Test Meals," Gastroenterology, vol. 108, No. 4, pp. 1048-1055, 1995.
Braden, B. et al., "$^{13}$C-breath tests: Current State of the Art and Future Directions," Dig. Liver Dis. 39(9):795-805 (2007).
Breen, Peter H. et al., "Measurement of blood $CO_2$ concentration with a conventional $Pco_2$ analyzer," Critical Care Medicine, vol. 24, No. 7, pp. 1215-1218, 1996.
Choi, M.G. et al., "Reproducibility and Simplification of $^{13}$C-Octanoic Acid Breath Test for Gastric Emptying of Solids," Am. J. Gastroenterol. 93:92-8 (1998).
Clough, Michael R.I., et al., "The Calcium Carbonate Breath Test, a noninvasive test of stimulated gastric acid secretion: preliminary communication," Eur J Gastroenterol Hepatol., vol. 21, No. 3, pp. 266-272, Mar. 2009.
Creasey, William A., et al., "The metabolism of uracil-2-$^{14}$C and the granulocyte response to endotoxin as indicators of the toxicity produced in patients receiving 5-fluorouracil," Clinical Pharmacology and Therapeutics, vol. 8, No. 2, pp. 273-282, 1967.
"Eiyo: Hyoka to Chiryo" Japanese Journal of Nutritional Assessment, vol. 29, No. 1, p. 37-40 (2012).
Fernandez-Salguero, Pedro, et al., "Correlation Between Catalytic Activity and Protein Content for the Polymorphically Expressed Dihydropyrimidine Dehydrogenase in Human Lymphocytes," Biochemical Pharmacology, vol. 50, No. 7, pp. 1015-1020, 1995.
Fleming, Ronald A., et al., "Correlation between Dihydropyrimidine Dehydrogenase Activity in Peripheral Mononuclear Cells and Systemic Clearance of Fluorouracil in Cancer Patients," Cancer Research, vol. 52, pp. 2899-2902, 1992.
Gan, K.H. et al., "Effect of Omeprazole 40 mg Once Daily on Intraduodenal and Intragastric pH in H. pylori-Negative Healthy Subjects," Digestive Diseases and Sciences, vol. 42, No. 11, pp. 2304-2309, 1997.
Geus, W.P., et al., "Pharmacodynamics and kinetics of omeprazole MUPS 20 mg and pantoprazole 40 mg during repeated oral administration in Helicobacter pylori-negative subjects," Alimentary Pharmacology & Therapeutics, vol. 14, pp. 1057-1064, 2000.
Ghoos, Y.F. et al., "Measurement of Gastric Emptying Rate of Solids by Means of a Carbon-Labeled Octanoic Acid Breath Test," Gastroenterology 104:1640-7 (1993).
Glerup, H. et al., "Gastric Emptying: A Comparison of Three Methods," Scand. J. Gastroenterol. 42:1182-86 (2007).

(56) References Cited

OTHER PUBLICATIONS

Herting, D.C. et al., "Absorption of Acetic Acid and Glycerol From the Rat Stomach," *Am. J. Physiol.* 187:224-26 (1956).

Hiroaki Kubo et al., Enhancement of Oral Bioavailability and Pharmacological Effect of 1-(3,4-Dimethoxyphenyl)-2,3-bis(methoxycarbonyl)-4-hydroxy-6,7,8-trimethoxynaphthalene(TA-7552), a New Hypocholesterolemic Agent, by Micronization in Co-ground Mixture with D-Mannitol, Biological and Pharmaceutical Bulletin, vol. 19, No. 5, 1996, pp. 741-747.

Inada, M. et al., "Pharmacokinetic modelling of [2-$^{13}$C]Uracil Metabolism in Normal and DPD-Deficient Dogs," *Nucleosides, Nucleotides, and Nucleic Acids* 25:1205-9 (2006).

Inada, M. et al., "Relationships Among Plasma [2-$^{13}$C]Uracil Concentrations, Breath $^{13}$CO$_2$ Expiration, and Dihypropyrimidine Dehydrogenase (DPD) Activity in the Liver in Normal and DPD-Deficient Dogs," *Drug Metabolism and Disposition* 33(6):381-87 (2005).

Irving, C.S. et al., "[$^{13}$C]bicarbonate kinetics in humans: intra- vs. interindividual variations," *Amer. J. Physiol.* 245(2):R190-R202 (1983).

Ito, S. et al., "Physiologically based pharmacokinetic modelling of the three-step metabolism of pyrimidine using $^{13}$C-uracil as an in vivo probe," *Br. J. Clin. Pharmacol.* 60:584-93 (2005).

Johnson, Martin R., et al., "Semi-automated radioassay for determination of dihydropyrimidine dehydrogenase (DPD) activity Screening cancer patients for DPD deficiency, a condition associated with 5-fluorouracil toxicity," *Journal of Chromatography B*, vol. 696, pp. 183-191, 1997.

Jones et al. Effect of fatty acid chain length and saturation on the gastrointestinal handling and metabolic disposal of dietary fatty acids in women, British Journal of Nutrition, 1999, vol. 81, pp. 37-43.

Kajiwara, "The Breath Test by Co$^2$ Analysis IV. $^{13}$ C-labelled Compounds for the Breath Test", Radioisotopes, 41, 47-50 (1992).

Kagaku no Ryoiki, Journal of Japanese Chemistry, vol. 107, pp. 149-163 (1975).

Karamanolis, G. et al., "Association of the Predominant Symptom With Clinical Characteristics and Pathophysiological Mechanisms in Functional Dyspepsia," *Gastroenterology* 130:296-303 (2006).

Kitagawa et al. "J. Smooth Muscle Res. (Jpn. Sec.) 6:J-129~J-138, 2002."

Lehman, K., "Acrylic Latices from Redisperable Powders for Peroral and Transdermal Drug Formulations," *Drug Development and Industrial Pharmacy*, vol. 12, No. 3, p. 265-287, 1986.

Iida, K. , et al., "Synthesis of $^{13}$ C-Labelled Compounds having a Urea Unit, and Observation of $^{13}$ C-Isotope Effect in Their Infrared Spectra" J. Labelled Cmpd. Radiopharmaceuticals—vol. XXXIX, No. 1. 1997, 39, 69-77.

Lu, Z. et al., "Decreased Dihydropyrimidine Dehydrogenase Activity in a Population of Patients with Breast Cancer: Implication for 5-Fluorouracil-based Chemotherapy," *Clin. Cancer Res.* 4:325-29 (1998).

Maes, B.D. et al., "$^{13}$C-Octanoic Acid Breath Test for Gastric Emptying Rate of Solids," *Gastroenterol.* 114:856-59 (1998).

Maes, B.D. et al., "Combined Carbon-13-Glycine/Carbon-14-Octanoic Acid Breath Test to Monitor Gastric Emptying Rates of Liquids and Solids," *J. Nuc. Med.* 35(5):824-31 (1994).

Mattison, L.K. et al., "The Uracil Breath Test in the Assessment of Dihydropyrimidine Dehydrogenase Activity: Pharmacokinetic Relationship between Expired $^{13}$CO$_2$ and Plasma [2-$^{13}$C]Dihydrouracil," *J. Am. Assoc. Cancer Res.* 12(2):549-55 (2006).

Mariani et al.; "Radionuclide Gastroesophageal Motor Studies", The Journal of Nuclear Medicine, vol. 45, No. 6, pp. 1004-1028, (2004).

Meineke, I., et al., "Evaluation of the $^{13}$CO$_2$ kinetics in humans after oral application of sodium bicarbonate as a model for breath testing," *European Journal of Clinical Investigation*, vol. 23, No. 2, pp. 91-96, 1993.

Mion, Francois; et al; "$^{13}$CO$_2$ breath test : comparison of isotope ratio mass spectrometry and non-dispersive infrared spectrometry results" Gastroenterologie Clinique et Biologique, 25, 375-379, 2001.

Nakada et al., "J. Smooth Muscle Res. (Jpn. Sec.) 6:J-75~J-91, 2002."

Ogata, Hiroyasu, et al., "Development and Evaluation of a New Peroral Test Agent GA-test for Assessment of Gastric Acidity," *J. Pharm. Dyn.*, vol. 7, pp. 656-664, 1984.

Quartero, A.O. et al., "Disturbed Solid-Phase Gastric Emptying in Functional Dyspepsia: A Meta-Analysis," *Dig. Disease and Sciences*. 43:2028-33 (1998).

B. Ravikumar et al., "Real-time assessment of postprandial fat storage in liver and skeletal muscle in health and type 2 diabetes", American Journal of Physiology, Endocrinology and Metabolism, vol. 288, No. 4, pp. E789-E797 (2005).

Sasaki, "Koki Kensa ni Okeru Antei Doitai Riyo", Nippon Isotope Hoshasen Sogo Kaigi Hobunshu, 18$^{th}$, pp. 610-617, (1988).

Sasaki, "5.1 Use of Stable Isotopes in Clinical Diagnoses," Kagaku no Ryoiki 107 "Use of Stable Isotopes in Medicine, Pharmacy and Biology," pp. 149-163 (1975) Nankodo.

Sanaka, M. et al. "Comparison Between Gastric Scintigraphy and the [$^{13}$C]-Acetate Breath Test with Wagner-Nelson Analysis in Humans," *Clin. Exp. Pharmacol. Physiol.* 33:1239-43 (2006).

Sanaka, M. et al., "The Wagner-Nelson Method Makes the [$^{13}$C]-Breath Test Comparable to Radioscintigraphy in Measuring Gastric Emptying of a Solid/Liquid Mixed Meal in Humans," *Clin. Exp. Pharmacol. Physiol.* 34:641-44 (2007).

Sato, T., et al., "Evaluation of Immunological Rapid Urease Testing for Detection of *Helicobacter pylori*," *European Journal of Clinical Microbiology & Infectious Diseases*, vol. 19, pp. 438-442, 2000.

Schneider, A.R. et al., "Total Body Metabolism of $^{13}$C-octanoic Acid Is Preserved in Patients with Non-Alcoholic Steatohepatitis, But Differs Between Women and Men," *Eur. J. Gastroenterol. Hepatol.* 17:1181-84 (2005).

Sidossis et al. Glucose and insulin-induced inhibition of fatty acid oxidation: the glucose-fatty acid cycle reversed, American Journal of Physiology, Apr. 1996, vol. 270, pp. E733-738.

Sjövall, H., et al., "Simultaneous Measurement of Gastric Acid and Bicarbonate Secretion in Man," *Scandinavian Journal of Gastroenterology*, vol. 24, No. 10, pp. 1163-1171, 1989.

Stranghellini, V. et al., "Risk Indicators of Delayed Gastric Emptying of Solids in Patients With Functional Dyspepsia," *Gastroenterol.* 110:1036-42 (1996).

Sugiyama, E. et al., "Desirable Pharmacokinetic Properties of $^{13}$C-uracil as a Breath Test Probe of Gastric Emptying in Comparison with $^{13}$C-acetate and $^{13}$C-octanoate in Rats," *Scand. J. Gastroenterol.* 44:1067-75 (2009).

Sumi, Satoshi, et al., "Automated screening system for purine and pyrimidine metabolism disorders using high-performance liquid chromatography," *Journal of Chromatography B*, vol. 672, pp. 233-239, 1995.

Sumi, Satoshi, et al., "Possible prediction of adverse reactions to fluorouracil by the measurement of urinary dihydrothymine and thymine," *International Journal of Molecular Medicine*, vol. 2, pp. 477-482, 1998.

Tack, J., "Gastric Motor Disorders," *Best Pract. Res. Clin. Gastroenterol.* 21:633-44 (2007).

Tazawa, S. et al., "KDR-5169, a New Gastrointestinal Prokinetic Agent, Enhances Gastric Contractile and Emptying Activities in Dogs and Rats," *Eur. J. Pharmacol.* 434:169-76 (2002).

Talley Nj et al. "Functional Gastroduodenal Disorders "Talley Nj et al., Gut 45 (Suppl 2): II 37-42, 1999.

The Merck Index, Merck Research Laboratories Division of Merck & Co., Inc., 2001, 13th Edition, pp. 1755-1756, No. 9918. Uracil.

Triplett, J.W., et al., "Synthesis of Carbon-13 Labelled Uracil, 6,7-Dimethyllumazine, and Lumichrome, Via a Common Intermediate: Cyanoacetylurea," *Journal of Labelled Compounds and Radiopharmaceuticals*, vol. 14, No. 1, pp. 35-41, 1978.

Tsuchiya, Masako et al., "Evaluation of a novel non-invasive $^{13}$C-giucose breath test for the identification of diabetes meilitus in cirrhotic patients." Hepatology Research, vol. 42, No. 12, pp. 1196-1201 (2012).

(56) References Cited

OTHER PUBLICATIONS

Van Kuilenburg, André B.P., et al., "Pitfalls in the Diagnosis of Patients with a Partial Dihydropyrimidine Dehydrogenase Deficiency," *Clinical Chemistry*, vol. 46, No. 1, pp. 9-17, 2000.

Votruba, S.B. et al., "Validation of Deuterium Labeled Fatty Acids for the Measurement of Dietary Fat Oxidation: a Method for Measuring Fat-Oxidation in Free-Living subjects," *Int. J. Obes. Relat. Metab. Disord.* 25:1240-45 (2001).

Wetzel, Klaus, et al., "$^{13}$C-Breath Tests in Medical Research and Clinical Diagnosis," *Fischer ANalysen Instrumente GmbH*, 4$^{th}$ Edition, May 2005. 66 pages.

Yen, J.L. et al., "Should DPD Analysis be Required Prior to Prescribing Pluoropyrimidines?" *Eur. J. Cancer* 43:1011-16 (2007).

Japanese articles S1-1 and S1-2, *Journal of Smooth Muscle Research*, vol. 14, No. 1, p. J-7, Jun. 11, 2010.

Japanese article, *Journal of the Vitamin Society of Japan*, vol. 74, No. 7, pp. 367-371, 2000.

Japanese article, *Journal of Japanese Society of Gastric Secretion Research*, vol. 31, pp. 5-8, 1999.

Japanese article, *Journal of Japanese Society of Gastric Secretion Research*, vol. 29, pp. 47-50, 1997.

Supplementary Partial European Search Report issued in EP Application No. 01941167, dated Nov. 1, 2004, 3 pages, as cited in related U.S. Appl. No. 13/817,349, filed Feb. 15, 2013.

Supplementary European Search Report for EP Application No. 01925887, dated May 25, 2007, 4 pages, as cited in related U.S. Appl. No. 13/817,349, filed Feb. 15, 2013.

Supplementary European Search Report issued in EP Application No. 11818231, dated Jan. 23, 2014, 6 pages, as cited in related U.S. Appl. No. 13/817,349, filed Feb. 15, 2013.

Supplementary European Search Report dated Oct. 7, 2016 for EP Application No. 14/763271.5.

European Search Report dated June 8, 2007 for European Application No. 01925887.0., as cited in the information disclosure Statement (dated) Jun. 27, 2011 in related U.S. Appl. No. 11/989,286, filed Jan. 24, 2008.

European Search Report dated Mar. 23, 2011 for European Application No. 07741475.3., as cited in the information disclosure Statement (dated) Jun. 27, 2011 in related U.S. Appl. No. 11/989,286, filed Jan. 24, 2008.

Extended European Search Report for EP Application No. 13831608.8 dated Mar. 30, 2016, which corresponds to related U.S. Appl. No. 14/776,543, filed Sep. 14, 2015 and U.S. Appl. No. 14/423,021, filed Feb. 20, 2015 (the present patent application).

International Search Report for International Application No. PCT/JP2007/058039, dated Jul. 10, 2007, and cited in related U.S. Appl. No. 12/295,631, filed Apr. 20, 2009.

International Search Report from the Japanese Patent Office for International Application No. PCT/JP2014/056699 dated Jun. 3, 2014.

Written Opinion of the International Searching Authority for International Application No. PCT/JP2006/314591, dated Aug. 22, 2006.

Office Action dated Oct. 11, 2012, in related U.S. Appl. No. 11/989,286, filed Jan. 24, 2008.

Office Action dated Apr. 9, 2013, in related U.S. Appl. No. 11/989,286, filed Jan. 24, 2008.

Office Action dated Oct. 7, 2016 for the corresponding U.S. Appl. No. 14/776,543.

Co-pending U.S. Appl. No. 14/776,543, filed Sep. 14, 2015.

U.S. Appl. No. 12/296,631, filed May 19, 2009.

Kasiske, et al., "The Zucker Rat Model of Obesity, Insulin Resistance, Hyperlipidemia, and Renal Injury," *Hypertension*, 1992, vol. 19 (1 Suppl), pp. I 110-I 115.

Boden, "Role of Fatty Acids in the Pathogenesis of Insulin Resistance and NIDDM," *Diabetes*, 1997, vol. 46, pp. 3-10.

Pick et al., "Role of Apoptosis in Failure of β-Cell Mass Compensation for Insulin Resistance and β-Cell Defects in the Male Zucker Diabetic Fatty Rat," *Diabetes*, 1998, vol. 47, pp. 358-364.

Griffin, et al., "Free Fatty Acid-Induced Insulin Resistance Is Associated With Activation of Protein Kinase C theta and Alterations in the Insulin Signaling Cascade," *Diabetes*, 1999, vol. 48, pp. 1270-1274.

Kelley, et al., "Skeletal muscle fatty acid metabolism in association with insulin resistance, obesity, and weight loss," *American Journal of Physiology*, 1999, vol. 227, pp. E1130-E1141.

Young, et al., "Impaired Long-Chain Fatty Acid Oxidation and Contractile Dysfunction in the Obese Zucker Rat Heart," *Diabetes*, 2002, vol. 51, pp. 2587-2595.

Mazumder et al., "Impaired Cardiac Efficiency and Increased Fatty Acid Oxidation in Insulin-Resistant ob/ob Mouse Hearts," *Diabetes*, 2004, vol. 53, pp. 2366-2374.

Nolan et al., "Beta cell compensation for insulin resistance in Zucker fatty rats: increased lipolysis and fatty acid signaling," *Diabetologia*, 2006, vol. 49, pp. 2120-2130.

Turner et al., "Excess Lipid Availability Increases Mitochondrial Fatty Acid Oxidative Capacity in Muscle," *Diabetes*, 2007, vol. 56, pp. 2085-2092.

Koves, et al., "Mitochondrial Overload and Incomplete Fatty Acid Oxidation Contribute to Skeletal Muscle Insulin Resistance," *Cell Metabolism*, 2008, vol. 7 pp. 45-56.

Savarino, et al., "The $^{13}$C urea breath test in the diagnosis of *Helicobacter pylori* infection," *Gut*, 1999, vol. 45(Suppl I), pp. I18-I22.

Office Action dated Apr. 27, 2017, U.S. Appl. No. 14/776,543.

Storlien, et al., "Influence of Dietary Fat Composition on Development of Insulin Resistance in Rats," *Diabetes*, vol. 40, pp. 280-289, Feb. 1991.

Office Action dated Feb. 2, 2018, U.S. Appl. No. 14/776,543.

Balasse, E.O. et al., "Operation of the 'Glucose-Fatty Acid Cycle' during Experimental Elevations of Plasma Free Fatty Acid Levels in Man," European Journal of Clinical Investigation, 1974, vol. 4, pp. 247-252.

Bonadonna, Riccardo C. et al., "Free Fatty Acid and Glucose Metabolism in Human Aging: Evidence for Operation of the Randle Cycle," American Journal of Physiology, 1994, vol. 266, E501-E509.

Hall, Susan E.H. et al., "Glucose and Free Fatty Acid Turnover in Normal Subjects and in Diabetic Patients Before and After Insulin Treatment," Diabetologia, 1979, vol. 16, pp. 297-306.

Laville, Martine et al., "Respective Role of Plasma Nonesterified Fatty Acid Oxidation and Total Lipid Oxidation in Lipid-Induced Insulin Resistance," Metabolism, May 1995, vol. 44, pp. 639-644.

Malmendier, C.L. et al., "Interrelations in the Oxidative Metabolism of Free Fatty Acids, Glucose, and Glycerol in Normal and Hyperlipemic Patients," Journal of Clinical Investigation, 1974, vol. 54, pp. 461-476.

McCue, M.D. et al., Tracking the Oxidative Kinetics of Carbohydrates, Amino Acids and Fatty Acids in the House Sparrow Using Exhaled $^{13}CO_2$.Journal of Experimental Biology, 2010, vol. 213, pp. 782-789.

Paul, Pavle et al., "Interrelationship of Free Fatty Acids and Glucose Metabolism in the Dog," American Journal of Physiology, 1966, vol. 211, No. 6, pp. 1313-1320.

Petrides, Alexander S. et al., "Effect of Physiologic Hyperinsulinemia on Glucose and Lipid Metabolism in Cirrhosis," Journal of Clinical Investigation, Aug. 1991, vol. 88, pp. 561-570.

Shaw, James H.F. et al., "Influence of p-hydroxputyrate Infusion on Glucose and Free Fatty Acid Metabolism in Dogs," American Journal of Physiology, 1984, vol. 247, E756-E764.

Steele, R. et al., "Plasma Glucose and Free Fatty Acid Metabolism in Normal and Long-Fasted Dogs," American Journal of Physiology, 1968, vol. 214, pp. 313-319.

Van Hall, Gerrit, "Correction Factors for 13C-Labelled Substrate Oxidation at Whole-Body and Muscle Level," Proceedings of the Nutrition Society, 1999, vol. 58, pp. 979-986.

Wolfe, Robert R. et al., "Glucose and FFA Kinetics in Sepsis: Role of Glucagon and Sympathetic Nervous System Activity," American Journal of Physiology, 1985, vol. 248, E236-E243.

(56) References Cited

OTHER PUBLICATIONS

Office Action for co-pending U.S. Appl. No. 14/776,543 dated Sep. 28, 2018.

* cited by examiner

METHOD FOR MEASURING CARBOHYDRATE METABOLISM ABILITY, AND COMPOSITION FOR USE IN SAID METHOD

TECHNICAL FIELD

The present invention relates to a method for measuring glucose metabolism ability of a subject, and a composition that is suitably used in the method. More specifically, the present invention relates to a method for measuring and monitoring glucose metabolism ability of a subject with a labeled C-breath test using $^{13}C$ etc., and a composition that is suitably used in the method. The present invention also relates to a method for determining a stage after onset or diabetes or/and a stage before onset of diabetes (hereafter, in the present specification, a stage after onset of diabetes and a stage before onset of diabetes may be collectively referred to as "diabetes stage") by measuring glucose metabolism ability of a subject with a labeled C-breath test.

BACKGROUND ART

In diagnosis of diabetes, it is common that first, primary screening is conducted with a urine glucose test or a fasting blood glucose level test, and, if such tests are positive a glucose tolerance test is performed to make a definite diagnosis. In recent years, HbA1C or fructosamine in the blood may also be tested before a glucose tolerance test using glucose.

However, the hitherto known methods, such as a urine glucose test and a fasting blood glucose level test, have the problem of low sensitivity since they show negative results of urine glucose and normal blood glucose levels for many diabetic patients, and thus overlook many cases of diabetic patients. Accordingly, the hitherto known methods are insufficient from the standpoint of preventive medicine for the reason that they cannot determine a state in which diabetes has not yet developed, but that is in a stage before onset of diabetes. In addition, although the glucose tolerance test using glucose is an excellent test, side effects caused by administration of a large amount of glucose have been indicated. Additionally, this test requires subjects to be restrained for several hours, and for blood to be repeatedly collected. Because this therefore imposes a great physical burden on subjects, this test can only actually be carried out on a limited number of subjects. Further, the results of HbA1C or fructosamine cannot be known until the next hospital visit, thus posing the drawback of insufficient rapidity.

Diagnosis of diabetes type (insulin dependent or noninsulin-dependent), determination of therapeutic strategy, and tests for evaluating the effect of treatment for diabetes are hitherto performed by mainly measuring blood insulin concentration, c-peptide in the blood or urine, blood glucose level in the glucose tolerance test using glucose, or change in blood insulin concentration over time. As described above, however, since the glucose tolerance test using glucose imposes a great physical burden on subjects, it is not actually conducted often. The result of blood insulin concentration or c-peptide in the blood or urine cannot be known until the next hospital visit; therefore, the rapidity of such tests is insufficient.

Meanwhile, applying measurement of $^{13}CO_2$ excreted in expired air as carbon dioxide after administration of $^{13}C$-labeled glucose, i.e., a labeled C-breath test, to diagnosis of diabetes has been proposed (see Patent Literature 1 to 3).

More specifically, Patent Literature 1 discloses a method for diagnosing the presence or absence of diabetes and the type of diabetes (type 1 diabetes or type 2 diabetes) by performing a breath test using glucose in which the carbon at a specific position is replaced by $^{13}C$, and determining the degree of increase in $^{13}CO_2$ concentration excreted in expired air. Patent Literature 2 and 3 discloses performing a breath test using $^{13}C$-labeled glucose as in Patent Literature 1 and diagnosing a diabetic patient, an insulin-resistant patient, or a impaired glucose tolerance patient by using, as an index, the ratio of $^{13}C$ to $^{12}C$ ($^{13}C/^{12}C$) in expired air that is lower than the ratio or a healthy subject, the ratio being calculated from the concentration of $^{13}CO_2$ excreted in the expired air.

However, none of these documents disclose or suggest that glucose metabolism ability of a subject can be detected with high accuracy with a labeled-C-breath test using glucose, allowing not only the stage of a patient in whom diabetes has developed to be determined and monitored, but also a stage before onset of diabetes.

Patent Literature 4 discloses a method in which $^2H$-labeled glucose is administered to a subject, the total amount of denterated water ($^2H_2O$) in the subject is measured, and a value obtained by dividing the total amount of deuterated water ($^2H_2O$) by the amount of insulin or the area under the curve of insulin concentration (insulin AUC) is used as an index to determine insulin resistance in the subject. Parent Literature 5 discloses a method in which the product of the area under the curve of insulin concentration (insulin AUC) and the area under the curve of glucose concentration (glucose AUC) ("insulin AUC×glucose AUC") is determined from the blood glucose level and insulin concentration measured after administration of a food for testing, and the obtained value is used as an index to determine insulin resistance in a subject.

As described above, these documents disclose that the area under the curve of insulin concentration (insulin AUC) is taken into consideration for evaluation of insulin resistance in a subject; however, none of these documents disclose or suggest that glucose metabolism ability of a subject can be detected with high accuracy with a labeled C-breath test using glucose, allowing not only a stage of a patient in whom diabetes has developed to be determined and monitored, but also a stage before onset of diabetes.

CITATION LIST

Patent Literature

PTL 1: JPH10-067689A
PTL 2: JP2002-513911A
PTL 3: JP2008-292506A
PTL 4: JP2006-543787A
PTL 5: JP2010-044093A

SUMMARY OF INVENTION

Technical Problem

An object of the present invention is to provide a method for detecting glucose metabolism ability of a subject rapidly and with high accuracy with a labeled C-breath test using isotope-labeled glucose. Another object of the present invention is to provide a method for determining and monitoring not only a stage of a patient in whom diabetes has developed, but also a stage before onset of diabetes.

Another object of the present invention is to provide a composition for measuring glucose metabolism ability for use in the above-described methods.

Solution to Problem

The present inventors conducted extensive research to achieve the above objects, and found that glucose metabolism ability of a subject can be measured rapidly and with high accuracy based on the behavior of the amount of isotope-labeled carbon dioxide ($CO_2$) excreted in expired air after administration of isotope-labeled glucose and the behavior of the abundance of carbon dioxide contained in the expired air (the ratio of labeled $CO_2$ amount to unlabeled $CO_2$ amount or the ratio of labeled $CO_2$ amount to total $CO_2$ amount), the abundance being calculated from the amount of isotope-labeled carbon dioxide ($CO_2$) excreted in the expired air. The present inventors also found that not only a stage of a patient in whom diabetes has developed can be determined and monitored over time by using the thus-obtained glucose metabolism ability of the subject as an index, but also a stage before onset of diabetes. Further, the present inventors found that the treatment effect of a drug (therapeutic agent for diabetes) on a diabetic patient can be determined and monitored over time by using the subject's glucose metabolism ability as an index. The present invention has been accomplished based on these findings.

More specifically, the present invention includes the following embodiments:

(1) Method for Measuring Glucose Metabolism Ability (1-1) A method for measuring glucose metabolism ability of a subject, comprising steps (a) and (b) below:
(a) administering a composition to a subject and collecting expired air, the composition comprising, as an active ingredient, glucose labeled with at least one isotope of C, wherein the glucose is converted in the body into labeled carbon dioxide that is excreted in expired air; and
(b) determining the ratio of labeled $CO_2$ amount to unlabeled $CO_2$ amount contained in the expired air or the ratio of labeled $CO_2$ amount to total $CO_2$ amount contained in the expired air.

As described below, step (b) can be performed by determining, for example, $\Delta$ % $^{13}C$ (amount of change in $^{13}C$ concentration: atom %) or $\Delta^{13}C$ value (amount of change in $\delta^{13}C$ value ‰.

(1-2) The method for measuring glucose metabolism ability according to (1-1), further comprising step (c) below:
(c) comparing "the ratio of labeled $CO_2$ amount to unlabeled $CO_2$ amount or total $CO_2$ amount contained in the expired air" obtained in the subject in step (b) (subject value) with "the ratio of labeled $CO_2$ amount to unlabeled $CO_2$ amount contained in the expired air or the ratio of labeled $CO_2$ amount to total $CO_2$ amount contained in the expired air" of a healthy subject (control value), and determining that the glucose metabolism ability of the former subject is decreased when the subject value is lower than the control value, and that the glucose metabolism ability of the former subject is enhanced when the subject value is higher than the control value.

(1-3) The method for measuring glucose metabolism ability according to (1-1) or (1-2), wherein the isotope is $^{13}C$.

(1-4) The method for measuring glucose metabolism ability according to any one of (1-1) to (1-3), wherein the dosage form of the composition is an oral dosage form or an injectable dosage form.

(1-5) The method for measuring glucose metabolism ability according to any one of (1-1) to (1-4), wherein a subject in a glucose-loaded state is subjected to step (a).

(1-6) The method for measuring glucose metabolism ability according to (1-5), wherein the subject in a glucose-loaded state is a subject that has taken, before step (a), a saccharide, or a food or beverage comprising a saccharide or a component that is metabolized to a saccharide.

(1-7) The method for measuring glucose metabolism ability according to (1-6), wherein the food or beverage is a liquid, semi-liquid, or solid food or beverage comprising at least one member selected from the group consisting of proteins (including semi-digested proteins), amino acids, fats, electrolytes, trace elements, and vitamins, in addition to a saccharide or a component that is metabolized to a saccharide.

(2) Method for Detecting a Stage After Onset of Diabetes and a Stage before Onset of Diabetes (2-1) A method for detecting a stage before onset of diabetes or/and a stage after onset of diabetes in a subject, using, as an index, glucose metabolism ability of the subject obtained by the method for measuring glucose metabolism ability according to any one of (1-1) to (1-7).

Hereafter, in the present specification, "a stage before onset of diabetes or/and a stage after onset of diabetes" may be collectively referred to as "diabetes stage".

(2-2) The method for detecting a diabetes stage according to (2-1), comprising the step of determining that a subject whose glucose metabolism ability is determined to be enhanced by the method for measuring glucose metabolism ability according to any one of (1-2) to (1-7) is in a stage before onset of diabetes.

More specifically, the method of the present invention can be restated as described in [2-a] to [2-g] below.

[2-a] A method for detecting a diabetes stage in a subject, the method comprising steps (a) to (c') below:
(a) administering a composition to a subject and collecting expired air, the composition comprising, as an active ingredient, glucose labeled with at least one isotope of G (labeled C-glucose), wherein the glucose is converted in the body into labeled carbon dioxide that is excreted in expired air;
(b) determining the ratio of labeled $CO_2$ amount to unlabeled $CO_2$ amount contained in the expired air or the ratio of labeled $CO_2$ amount to total $CO_2$ amount contained in the expired air; and
(c') comparing "the ratio of labeled $CO_2$ amount to unlabeled $CO_2$ amount contained in the expired air or the ratio of labeled $CO_2$ amount to total $CO_2$ amount contained in the expired air" ($\Delta$ % $^{13}C$(atom %) or $\Delta^{13}C$ value(‰)) obtained in the subject in step (b) (subject value) with "the corresponding ratio of labeled $CO_2$ amount to unlabeled $CO_2$ amount contained in the expired air or the corresponding ratio of labeled $CO_2$ amount to total $CO_2$ amount contained in the expired air" ($\Delta$ % $^{13}C$(atom %) or $\Delta^{13}C$ value(‰)) of a healthy subject (control value), and determining that diabetes has developed in the for/tier subject when the subject value is lower than the control value, and that the former subject is in a stage before onset of diabetes when the subject value is higher than the control value.

[2-b] The method according to [2-a], wherein the isotope is $^{13}C$.

[2-c] The method according to [2-a] or [2-b], wherein the dosage form of the composition is an oral dosage form or an injectable dosage form.

[2-d] The method according to any one of [2-a] to [2-c], wherein a subject in a glucose-loaded state is subjected to step (a).

[2-f] The method according to [2-d], wherein the subject in a glucose-loaded state is a subject that has taken, before step (a) a saccharide, or a food or beverage comprising a saccharide or a component that is metabolized to a saccharide.

[2-g] The method according to [2-f], wherein the food or beverage is a liquid, semi-liquid, or solid food or beverage comprising at least one member selected from the group consisting of proteins (including semi-digested proteins), amino acids, fats, electrolytes, trace elements, and vitamins, in addition to a saccharide or a component that, is metabolized to a saccharide.

In addition to the above method, the method for detecting a diabetes stage of the present invention can also be performed by the methods described in (2-3) to (2-6) below.

(2-3) The method according to (2-1), wherein [an area under the $\Delta^{13}C$(‰)-expired air collection time t curve ($\Delta^{13}C$(‰)$AUC_t$] or a $\Delta^{13}C$(‰) value at at least one point in time (t) after test sample administration ($\Delta^{13}$(‰)$_t$) is used as an index of glucose metabolism ability of a subject obtained by the method for measuring glucose metabolism ability according to any one of (1-1) to (1-6), and a stage before onset of diabetes or/and a stage after onset of diabetes in the subject is detected from a correlation between a blood glucose level of the subject, and a value obtained by dividing the $\Delta^{13}C$(‰)$AUC_t$ or the $\Delta^{13}C$(‰)$_t$ by an insulin concentration of the subject ("$\Delta^{13}C$(‰) $AUC_t$/insulin" or "$\Delta^{13}C$(‰)$_t$/insulin").

(2-4) The method according to (2-3), wherein the at least one point in time (t) after test sample administration is at least one point in time within 120 minutes after test sample administration.

(2-5) The method according to (2-3) or (2-4), wherein the at least one point in time (t) after test sample administration is at least one point in time 10 minutes or more after test sample administration.

(2-6) The method according to any one of (2-3) to (2-5), comprising the step of determining that a subject is in a step before onset of diabetes or in a stage after onset of diabetes when the "$\Delta^{13}C$(‰)$AUC_t$/insulin" or "$\Delta^{13}C$(‰)$_t$/insulin" of the subject is lower than the "$\Delta^{13}C$(‰)$AUC_t$/insulin" or "$\Delta^{13}C$(‰)$_t$/insulin" of a healthy subject.

(3) Method for Detecting the Effect of Treatment for Diabetes on a Diabetic Patient (3-1) A method for detecting the effect of treatment for diabetes on a diabetic patient receiving the treatment for diabetes, using, as an index, glucose metabolism ability of the diabetic patient obtained by the method for measuring glucose metabolism ability according to any one of (1-1) to (1-6).

(3-2) The method according to (3-1), comprising the step of comparing glucose metabolism ability of a subject measured before treatment for diabetes with glucose metabolism ability of the subject measured after the treatment for diabetes, and determining that the treatment for diabetes is effective in the subject based on an increase in glucose metabolism ability after the treatment for diabetes compared with glucose metabolism ability before the treatment for diabetes.

More specifically, the method of the present invention can be restated as described in [3-a] to [3-g] below.

[3-a] A method for detecting the effect of treatment for diabetes on a diabetic patient, the method comprising the steps (a'), (b), and (d) below:

(a') administering a composition to the subject before and after the treatment for diabetes and collecting expired air, the composition comprising, as an active ingredient, glucose labeled with at least one isotope of C (labeled C-glucose), wherein the glucose is converted in the body into labeled carbon dioxide that is excreted in expired air;

(b) determining the ratio of labeled $CO_2$ amount to unlabeled $CO_2$ amount contained in the expired air before and after the treatment for diabetes, or the ratio of labeled $CO_2$ amount to total $CO_2$ amount contained in the expired air before and after the treatment for diabetes; and (d) comparing "the ratio of labeled $CO_2$ amount to unlabeled $CO_2$ amount contained in the expired air or the ratio of labeled $CO_2$ amount to total $CO_2$ amount contained in the expired air" ($\Delta$ % $^{13}C$(atom %) or $\Delta^{13}$ C value (‰)) obtained in the subject after the treatment for diabetes in step (b) (subject value) with "the corresponding ratio of labeled $CO_2$ amount to unlabeled $CO_2$ amount contained in the expired air or the corresponding ratio of labeled $CO_2$ amount to total $CO_2$ amount contained in the expired air" ($\Delta$ % $^{13}C$(atom %) or $\Delta^{13}C$ value (‰)) obtained in the subject before the treatment for diabetes in step (b) (control value), and determining that the treatment for diabetes is effective in the subject when the subject value is higher than the control value, and that the treatment for diabetes is not effective in the subject when the subject value is the same as or lower than the control value.

[3-b] The method according to [3-a], wherein the isotope is $^{13}C$.

[3-c] The method according to [3-a] or [3-b], wherein the dosage form of the composition is an oral dosage form or an injectable dosage form.

[3-d] The method according to any one of [3-a] to [3-c], wherein a subject in a glucose-loaded state is subjected to step (a').

[3-f] The method according to [3-d], wherein the subject in a glucose-loaded state is a subject that has taken, before step (a'), a saccharide, or a food or beverage comprising a saccharide or a component that is metabolized to a saccharide.

[3-g] The method according to [3-f], wherein the food or beverage is a liquid, semi-liquid, or solid food or beverage comprising at least one member selected from the group consisting of proteins (including semi-digested proteins), amino acids, fats, electrolytes, trace elements, and vitamins, in addition to a saccharide or a component that is metabolized to a saccharide.

(4) Composition for Measuring Glucose Metabolism Ability (4-1) A composition for measuring glucose metabolism ability, the composition comprising, as an active ingredient, glucose labeled with at least one isotope of C, wherein the glucose is converted in the body into labeled carbon dioxide that is excreted in expired air.

(4-2) The composition for measuring glucose metabolism ability according to (4-1), wherein the isotope is $^{13}C$.

(4-3) The composition for measuring glucose metabolism ability according to (4-1) or (4-2), wherein the dosage form of the composition is an oral dosage form or an injectable dosage form.

(5) Use of Labeled G-Glucose (5-1) Use of glucose labeled with at least one isotope of C for the production of a composition for measuring glucose metabolism ability with a breath test, (composition for measuring glucose metabolism ability), wherein the glucose is converted in the body into labeled carbon dioxide that is excreted in expired air.

(5-2) The use according to (5-1), wherein the measurement of glucose metabolism ability is performed by the method according to (1-6) or (1-7).

(5-3) Use of glucose labeled with at least one isotope of C for the production of a composition for determining a stage before onset of diabetes or/and a stage after onset of diabetes with a breath test (composition for determining a diabetes stage), wherein the glucose is converted in the body into labeled carbon dioxide that is excreted in expired air.

(5-4) The use according to (5-3), wherein the determination of a stage before onset of diabetes or/and a stage after onset of diabetes is performed by the method according to any one of (2-1) to (2-6) and (2-a) to (2-g).

(5-5) Use of glucose labeled with at least one isotope of G for the production of a composition for detecting the effect of treatment for diabetes on a diabetic patient with a breath test (composition for detecting the effect of treatment for diabetes), wherein the glucose is converted in the body into labeled carbon dioxide that is excreted in expired air.

(5-6) The use according to (5-5), wherein the detection of the effect of treatment for diabetes is performed by the method according to any one of (3-1), (3-2), and (3-a) to (3-g).

(6) Use of Labeled C-glucose or Composition Comprising Labeled C-glucose (6-1) Glucose labeled with at least one isotope of C or a composition comprising the glucose as an active ingredient for use in measurement of glucose metabolism ability with a breath test, wherein the glucose is converted in the body into labeled carbon dioxide that is excreted in expired air.

(6-2) The glucose or composition according to (6-1), wherein the measurement of glucose metabolism ability is performed by the method according to (1-6) or (1-7).

(6-3) Glucose labeled with at least one isotope of C or a composition comprising the glucose as an active ingredient for use in determination of a stage before onset of diabetes or/and a stage after onset of diabetes with a breath test, wherein the glucose is converted in the body into labeled carbon dioxide that is excreted in expired air.

(6-4) The glucose or composition according to (6-3), wherein the determination of a stage before onset of diabetes or/and a stage after onset of diabetes is performed by the method according to any one of (2-1) to (2-6) and (2-a) to (2-g).

(6-5) Glucose labeled with at least one isotope of C or a composition comprising the glucose as an active ingredient for use in detection of the effect of treatment for diabetes on a diabetic patient with a breath test, wherein the glucose is converted in the body into labeled carbon dioxide that is excreted in expired air.

(6-6) The glucose or composition according to (6-5), wherein the detection of the effect of treatment for diabetes is performed by the method according to any one of (3-1), (3-2), and (3-a) to (3-g).

Advantageous Effects of Invention

The method of the present invention makes it possible to measure and evaluate glucose metabolism ability of a subject rapidly and with high accuracy. The accuracy and rapidity can be further improved by performing the method of the present invention on a subject under glucose-loaded conditions and/or employing intravenous administration, rather than oral administration, as the administration route of labeled C-glucose as a test substance.

In addition, the method of the present invention makes it possible to determine not only a stage of a patient in whom diabetes has developed, but also whether a subject is in a stage-before onset of diabetes, and monitor the state (diabetes condition including a state before onset of diabetes) over time, by using the thus-measured glucose metabolism ability of the subject as an index. In particular, the diabetes stage can be determined and evaluated in a short period of time, i.e., preferably within 60 minutes and more preferably within 30 minutes after the start of a test (administration of a composition comprising, as an active ingredient, glucose labeled with at least one isotope of C). Therefore, the method of the present invention can reduce a subject's physical or mental burden while making it unnecessary to restrain the subject for a long period of time.

Further, the method of the present invention makes it possible to determine the effect of treatment for diabetes on a diabetic patient receiving the treatment for diabetes and monitor the effect of the treatment for diabetes over time, by using glucose metabolism ability of the subject as an index. According to the present invention, the effect of treatment for diabetes can be determined and evaluated in a short period of time, i.e., preferably within 120 minutes, more preferably within 60 minutes, and still more preferably within 30 minutes after the start of a test (administration of a composition comprising, as an active ingredient, glucose labeled with at least one isotope of C). Therefore, the method of the present invention can, in determining the effect of treatment for diabetes, reduce a subject's physical or mental burden, while making it unnecessary to restrain the subject for a long period of time.

BRIEF DESCRIPTION OF DRAWINGS

FIG. 1 shows changes in $\Delta^{13}C(‰)$ in expired air measured after the $^{13}$C-glucose solutions were individually administered to each of the four groups of rats (1-$^{13}$C-Glc-administration group, 2-$^{13}$C-Glc-administration group, 3-$^{13}$C-Glc-administration group, and U-$^{13}$C-Glc-administration group). In FIG. 1, the $\Delta^{13}C(‰)$ in the expired air is plotted on the ordinate, whereas the expired air collection time (t) (minutes) after the administration of each $^{13}$C-glucose solution is plotted on the abscissa.

FIG. 2 snows changes in $\Delta^{13}C(‰)$ in expired air measured after a U-$^{13}$C-glucose solution for oral administration was administered to four groups of rats (Group A: healthy group, Group B: diabetes severe onset group, Group C: diabetes moderate onset group, and Group D; diabetes pre-onset stage group; the same applies to FIGS. 3 and 4 below). In FIG. 2, the $\Delta^{13}C$ (‰) in the expired air is plotted on the ordinate, whereas the expired air collection time (t) (minutes) after the administration of the U-$^{13}$C-glucose solution for oral administration is plotted on the abscissa. The same applies to FIGS. 5 to 13 below.

FIG. 3 shows the correlation between, each "blood glucose level (mg/dL)" of the four groups of rats (on the abscissa) and each value obtained by dividing the [area under the $\Delta^{13}C(‰)$-expired air collection time (120 minutes) curve (AUC)] of each group by the insulin concentration (ng/mL) of each group "$AUC_{120}$/insulin (‰·min·mL/ng)" (on the ordinate).

FIG. 4 shows the correlation between each "blood glucose level (mg/dL)" of the four groups of rats (on the abscissa) and each value obtained by dividing the $\Delta^{13}C(‰)$ (10 minutes) of each group by the insulin concentration (ng/mL) of each group "$\Delta^{13}C(‰)$ (10 minutes)/insulin (‰·min·mL/ng)" (on the ordinate).

FIG. 5 shows changes in $\Delta^{13}C(‰)$ in expired air measured after a U-$^{13}$C-glucose solution for oral administration was administered to rats (ZDF Fatty and ZDF lean) at different weeks of age.

FIG. 6 shows changes in $\Delta^{13}C(‰)$ in expired air measured after an aqueous U-$^{13}$C-glucose solution (50 μmol/4 mL/kg) was orally administered to Group 1 (control group) and Group 2 (diabetes group) under fasting conditions.

FIG. 7 shows changes in $\Delta^{13}C(‰)$ in expired air measured after an aqueous glucose solution (450 mg/4 mL/kg) and an aqueous U-$^{13}$C-glucose solution (50 μmol/4 mL/kg) were orally administered simultaneously to Group 1 (control group) and Group 2 (diabetes group).

FIG. 8 shows changes in $\Delta^{13}C(‰)$ in expired air measured after an aqueous U-$^{13}$C-glucose solution (50 μmol/4 mL/kg) was orally administered to Group 1 (control group) and Group 2 (diabetes group) 30 minutes after oral administration of an aqueous glucose solution (450 mg/4 mL/kg).

FIG. 9 shows changes in $\Delta^{13}C(‰)$ in expired air measured after an aqueous U-$^{13}$C-glucose solution (50 μmol/4 mL/kg) was intravenously administered to Group 1 (control group) and Group 2 (diabetes group) 30 minutes after oral administration of an aqueous glucose solution (450 mg/4 mL/kg).

FIG. 10 shows changes in $\Delta^{13}C(‰)$ in expired air measured after an aqueous U-$^{13}$C-glucose solution (50 μmol/4 mL/kg) was intravenously administered to Group 1 (control group) and Group 2 (diabetes group) 30 minutes after oral administration of an aqueous glucose solution (2 g/4 mL/kg).

FIG. 11 shows changes in $\Delta^{13}C(‰)$ in expired air measured after an aqueous U-$^{13}$C-glucose solution (50 μmol/4 mL/kg) was intravenously administered to Group 1 (control group) and Group 2 (diabetes group) 30 minutes after oral administration of an enteral nutrition agent (protein and amino acid preparation; trade name: "Racol (registered trademark) Liquid for Enteral Use") in an amount of 4 mL/kg.

FIG. 12 shows changes in $\Delta^{13}C(‰)$ before administration of a therapeutic agent for diabetes (no treatment) and changes in $\Delta^{13}C(‰)$ after administration of a therapeutic agent for diabetes (metformin) in three groups of rats (Group A: healthy group. Group B: diabetes severe onset group, and Group C: diabetes moderate onset group).

FIG. 13 shows the expired air patterns (changes in the $\Delta^{13}C(‰)$) of the groups of rats (control group: -■-, type 1 diabetes group: -□-, insulin-administered 4 h-diabetes group: -Δ-, and insulin-administered 24 h-diabetes group: -◆-).

Figure 1:
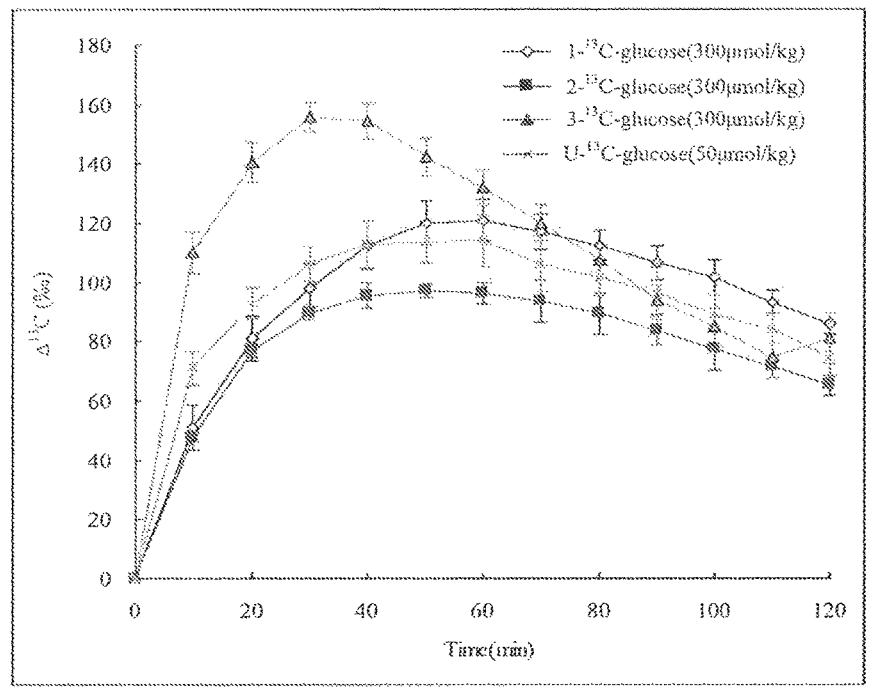
FIG. 1 illustrates the results of Experimental Example 1.

DESCRIPTION OF EMBODIMENTS (I) Description of Terms and Analysis Methods Relating to Labeled C-Breath Test The method for measuring glucose metabolism ability of the present invention is based on using a labeled C-breath test, such as a $^{13}$C-breath test. Thus, before description of the present invention, terms and analysis methods thereof relating to a labeled C-breath test are described (Tsuneo Matsubayashi, Wataru Matsuyama, Society for Medical Application of Carbon Thirteen. $^{13}$C-Koki Shiken no Jissai, Kiso to Jissentaki Oyo, Dai 8 Kou: $^{13}$C-Koki Shiken Data Kaisekiho [Practice of $^{13}$C-breath tests, basis and practical application, section 8: $^{13}$C-breath test data analysis method], pp. 102-111).

Here, $^{13}$C is described as an example of "at least one isotope of C or O" used in the present invention.

(1) $\delta^{13}$C Value (‰)

Abundances of isotopes are expressed in terms of isotopic ratio (R) in which the most abundant isotope of the same element is used as the denominator. Thus, with respect to carbon-13 ($^{13}$C), R value is expressed by the following formula in which carbon-12 ($^{12}$C) is used as the denominator.

$$R = {}^{13}C/{}^{12}C \qquad \text{(Formula 1)}$$

Since R is a very small numerical value, it is difficult to directly measure. When a mass spectrometer is used for more accurate quantification, comparison with a standard substance is always performed. The measurement result is represented by δ value defined by the following formula.

$$\delta^{13}C = ([R_{SAM}/R_{STD}] - 1) \times 1000 \qquad \text{(Formula 2)}$$

$\delta^{13}$C: $\delta^{13}$C value (‰)
$R_{SAM}$: abundance of $^{13}$C in sample gas
$R_{STD}$: abundance of $^{13}$C in standard gas When carbon dioxide derived from limestone (PDB) is used as standard gas, $R_{STD}$ is $R_{PDB} = 0.0112372$.

(2) $\Delta^{13}$C Value (‰)

"$\Delta^{13}$C value (‰)" means a value ($\Delta^{13}$) obtained by subtracting the $\delta^{13}$C value before administration of a reagent (i.e., naturally occurring δ value of $^{13}$C) as a background from the $\delta^{13}$C value after administration of the reagent, as shown in the following formula.

$$\Delta^{13}C(‰) = (\delta^{13}C)_t - (\delta^{13}C)_0 \qquad \text{(Formula 3)}$$

$\Delta^{13}C(‰)$: amount of change in $\delta^{13}$C value (‰)
$(\delta^{13}C)_t$: $\delta^{13}$C value t hr. after reagent administration (‰)
$(\delta^{13}C)_0$: $\delta^{13}$C value 0 hr. before reagent administration (‰)

(3) $^{13}$C Concentration in Expired Air (% $^{13}$C: atom %)

The $^{13}$C concentration in expired air (% $^{13}$C: atom %) is defined by the following formula.

$$\%^{13}C = [{}^{13}C/({}^{13}C + {}^{12}C)] \times 100$$

To convert the relative value $\delta^{13}$C defined in (1) into the $^{13}$C concentration (%) in the total carbon, which is a common concept of concentration, the following method can be used.

First, the numerator and denominator on the right side of the above formula are divided by $^{12}$C, and converted into R based on (Formula 1), The following formula is thus obtained.

$$\%^{13}C = [R/(R+1)] \times 100 \qquad \text{(Formula 4)}$$

If $R_{SAM}$ obtained in (Formula 2) is substituted into R above and rearranged, the following formula is obtained.

The $^{13}C$ concentration (% $^{13}C$) can be expressed by using the $\delta^{13}C$ value.

$$\% \ ^{13}C = \{[(\delta^{13}C/1000)+1] \times R_{PDB} \times 100\}/([[(\delta^{13}C/1000)+1] \times R_{PDB}]+1) \quad \text{(Formula 5)}$$

% $^{13}C$: $^{13}C$ concentration (atom %)
$\delta^{13}C$: $\delta^{13}C$ value (‰)
$R_{PDB}$: abundance of $^{13}C$ in PDB standard gas=0.0112372

(4) Amount of Change in $^{13}C$ Concentration ($\Delta$ % $^{13}C$)

As defined in the following formula, the amount of change in $^{13}C$ concentration (% $^{13}C$) in expired air ($\Delta$ % $^{13}C$) is determined by subtracting the $^{13}C$ concentration 0 hr. before administration [(% $^{13}C)_0$] from the $^{13}C$ concentration t hr. after administration [(% $^{13}C)_t$].

$$\Delta \%^{13}C = (\% \ ^{13}C)_t - (\% \ ^{13}C)_0 \quad \text{(Formula 6)}$$

$\Delta$ $^{13}C$: amount of change in $^{13}C$ concentration (atom %)
(% $^{13}C)_t$: $^{13}C$ concentration t hr after reagent administration (atom %)
(% $^{13}C)_0$: $^{13}C$ concentration 0 hr. before reagent administration (atom %)

(5) Relation between $\Delta^{13}C$ Value (‰) and Amount of Change in $^{13}C$ Concentration ($\Delta$ % $^{13}C$)

The natural abundance (R) of $^{13}C$ is about 0.011, and even when a labeled reagent is administered, the increased amount in expired air is only about +0.001 to 0.002. Thus, the natural abundance can be regarded as R→0, and (Formula 4), which expresses % $^{13}C$ by using R, can be approximated by the following formula.

$$\% \ ^{13}C = [R/(R+1)] \times 100 \approx R \times 100$$

Using this approximate expression, an approximation that determines the $^{13}C$ concentration (Formula 7) can be obtained as follows: first, $R_{SAM}$ determined by (Formula 2), which defines $\delta^{13}C$, substituted into R in the above formula, and rearranged.

$$\% \ ^{13}C = [(\delta^{13}C/1000)+1] \times R_{PDB} \times 100 \quad \text{(Formula 7)}$$

When this is substituted into (Formula 6), $\Delta$ % $^{13}C$ can be calculated from $\Delta^{13}C$, as shown in (Formula 8) below.

$$\begin{aligned}\Delta \%^{13}C &= (\%^{13}C)_t - (\%^{13}C)_0 \quad \text{(Formula 8)}\\ &= \{[(\delta^{13}C)_t - (\delta^{13}C)_0]/1000\} \times R_{PDB} \times 100 \\ &= (\Delta^{13}C \times R_{PDB})/10\end{aligned}$$

$\Delta$ % $^{13}C$: amount of change in $^{13}C$ concentration (atom %)
$\Delta^{13}C$: amount of change in $\delta^{13}C$ value (‰)
$R_{PDB}$: abundance of $^{13}C$ in PDB standard gas=0.0112372

(II) Composition for Measuring Glucose Metabolism Ability

The composition for measuring glucose metabolism ability of the present invention comprises, as an active ingredient, glucose labeled with at least one isotope of C, wherein the glucose is converted in the body into labeled $CO_2$ gas that is excreted in expired air. The labeled C-glucose used in the present invention has a feature such that, after being administered to a subject, the labeled C-glucose is metabolized according to glucose metabolism ability in the body and excreted in expired air in the form of carbon dioxide containing labeled C, which reflects the degree of glucose metabolism ability of the subject.

There is no particular limitation on isotopes used in labeling carbon atoms of glucose, and specific examples include $^{13}C$ and $^{14}C$. Such isotopes may be radioactive or non-radioactive; however, from the standpoint of safety, non-radioactive isotopes are preferable. For example, $^{13}C$ is desirable for use as such an isotope.

The isotope-labeled glucoses is labeled in such a manner that at least a portion of the $CO_2$ formed through the glucose metabolic pathway is isotope-labeled. Examples of such glucose include compounds in which the carbon atom at at least one of the 1-position or the 6-position, the 2-position or the 5-position, and the 3-position or the 4-position of glucose is labeled with an isotope. Specific examples include 1-$^{13}C$-labeled glucose, 2-$^{13}C$-labeled glucose, and 3-$^{13}C$-labeled glucose. Glucose in which all of the carbon atoms at the 1-, 2-, 3-, 4-, 5-, and 6-positions are isotope-labeled may be used. As indicated in Experimental Example 1 described later, glucose in which the carbon atom at the 3-position or the 4-position is isotope-labeled (e.g., 3-$^{13}C$-labeled glucose and 4-$^{13}C$-labeled glucose) and glucose in which all of the carbon atoms at the 1-, 2-, 3-, 4-, 5-, and 6-positions are isotope-labeled, are preferable from the standpoint of the speed of the rise of "$\Delta^{13}C$(‰)," i.e., the speed of excretion in expired air in the form of $^{13}CO_2$ after $^{13}C$-labeled glucose administration.

There is no particular limitation on the method for labeling compounds such as glucose with isotopes such as $^{13}C$, $^{14}C$, and $^{18}O$, and a wide variety of commonly used methods may be employed (Sasaki, "5.1 *Antei Doitai no Rinsho Shindan heno Oyo* [5.1 Application of Stable Isotopes in Clinical Diagnosis]": *Kagaku no Ryoiki* [Journal of Japanese Chemistry] 107, "*Antei Doitai no I•Yakugaku Seibutsugaku heno Oyo* [Application of Stable Isotopes in Medicine, Pharmacy, and Biology]," pp. 149-163 (1975) Nankodo: Kajiwara, RADIOISOTOPES, 41, 45-48 (1992), etc.). Such isotope-labeled compounds, particularly $^{13}C$-labeled-glucose described in the Examples, are commercially available as conveniently usable commercial products.

There is no particular limitation on the composition of the present invention in terms of its form, components other than the labeled C-glucose, proportion of each component, preparation method of the composition, etc., as long as the labeled C-glucose is absorbed in the body after administration, and excreted in expired air in the form of labeled carbon dioxide after metabolism.

For example, the form of the composition may be an oral dosage form or an intravenous dosage form. Examples of oral dosage forms include any oral dosage forms, such as solutions (including syrup), suspensions, emulsions and Like liquids; tablets (with and without coating), chewable tablets, capsules, pills, pulvis (powders), fine particles, granules, and like solids. Examples of intravenous dosage forms include any intravenous dosage forms, such as injections and drops (in liquid suspension, or emulsion form). The form of the composition is preferably an oral dosage form, which is a non-invasive measurement method, and more preferably, from the standpoint of obtaining high measurement accuracy, as indicated in Experimental Example 4, an intravenous dosage form.

The application of the composition of the present invention is not limited to a formulation such as a pharmaceutical preparation, as long as the composition contains the labeled C-glucose and does not adversely affect, the effects of the present invention. The labeled C-glucose may be combined with any foodstuff and formed into solid food, fluid food, or liquid food.

The composition of the present invention may substantially consist of the labeled C-glucose, which is an active ingredient; however, as long as the effects of the present invention are not adversely affected, any pharmaceutically acceptable carriers and/or additives that are generally used in this field may be added as other components according to a pharmaceutical form (dosage form).

In this case, there is no particular limitation on the amount of the labeled C-glucose contained as an active ingredient. For example, the amount of the labeled C-glucose is in the range of 1 to 95 wt % based on the total weight (100 wt %) of the composition, and is suitably controlled within this range.

When the composition of the present invention is prepared in liquid, suspension, or emulsion form, for example, drops or injections, various carriers and/or additives suitable to such forms may be used in addition to purified water or water for injection. Examples of additives include additives commonly used, such as tonicity-adjusting agents (e.g., sodium chloride etc.), pH adjusters (e.g., hydrochloric acid, sodium hydroxide, etc.), buffers (e.g., boric acid, sodium monohydrogen phosphate, sodium dihydrogen phosphate, etc.), preservatives (e.g., benzalkonium chloride etc.), and thickeners (e.g., carboxyvinyl polymers etc.).

When the composition of the present invention is formed into, for example, tablets, chewable tablets, capsules, pills, pulvis (powders), fine particles, granules and like solid forms, various carriers and/or additives suitable for such forms may be used.

Examples of usable carriers or additives include lactose, sucrose, dextrin, mannitol, xylitol, sorbitol, erythritol, calcium dihydrogen phosphate, sodium chloride, glucose, urea, starch, calcium carbonate, kaolin, crystalline cellulose, silicic acid, and like excipients; water, ethanol, simple syrup, glucose liquid, starch liquid, gelatin liquid, carboxymethyl cellulose, sodium carboxymethyl cellulose, shellac, methyl cellulose, hydroxypropylmethyl cellulose, hydroxypropyl cellulose, potassium phosphate, polyvinyl alcohol, polyvinyl pyrrolidone, dextrin, pullulan, and like binders; dry starch, sodium alginate, agar powder, laminaran powder, sodium bicarbonate, calcium carbonate, polyoxyethylene sorbitan fatty acid esters, sodium lauryl sulfate, monoglyceride stearate, starch, lactose, carmellose calcium, low substituted hydroxypropyl cellulose, carmellose, croscarmellose sodium, sodium carboxymethyl starch, crospovidone, and like disintegrators; sucrose, stearic acid, cacao butter, hydrogenated oil, and like disintegration inhibitors; polysorbate 80, quaternary-ammonium base, sodium lauryl sulfate, and like absorption promoters; glycerin, starch, and like humectants; starch, lactose, kaolin, bentonite, colloidal silicic acid, and like adsorbents; purified talc, stearate, boric acid powder, polyethylene glycol, colloidal silicic acid, sucrose fatty acids, hardened oil, and like lubricants; citric acid, anhydrous citric acid, sodium citrate, sodium citrate dihydrate, anhydrous sodium monohydrogenphosphate, anhydrous sodium dihydrogenphosphate, sodium hydrogen phosphate, and like pH adjusters; iron oxide, β carotene, titanium oxide, food colors, copper chlorophyll, riboflavin, and like coloring agents; and ascorbic acid, sodium chloride, various sweeteners, and like corrigents.

Tablets may be provided with an ordinary coating, if necessary. Examples thereof include sugar-coated tablets, gelatin-coated tablets, film-coated tablets, double-coated tablets, multi-coated tablets, etc. Capsules are prepared in a commonly employed method, i.e., mixing the isotope-labeled glucose, which is an active ingredient, with various carriers mentioned above and placing it in a hard gelatin capsule, a soft capsule, etc.

The composition of the present invention is used as a sample that is administrated to a subject in the measurement method described later (test sample). More specifically, the composition of the present invention is used as a test sample to be administered for measuring glucose metabolism ability in a subject. The composition of the present invention is also used as a test sample to be administered for measuring and determining a stage before onset of diabetes or/and a stage after onset of diabetes in a subject. Further, the composition of the present invention is used as a test sample to be administered for determining and monitoring the effect of treatment for diabetes on a diabetic patient.

All of these measurement methods are performed by administering the composition of the present invention to a subject (including a human and an animal), collecting expired air measuring the abundance of carbon dioxide contained in the expired air (the ratio of labeled $CO_2$ amount to unlabeled $CO_2$ amount or the ratio of labeled $CO_2$ amount to total $CO_2$ amount), and using the abundance as an index. The details are described in (III) below.

When the form of the composition for measuring glucose metabolism ability of the present invention is an oral dosage form or an intravenous dosage form (injections or drops), the amount of the labeled C-glucose (active ingredient) contained in the composition may be suitably selected according to each case. In either case, the dose may be adjusted so that the amount of the labeled C-glucose (active ingredient) is in the range of 5 mg/body to 50 g/body, and preferably 10 mg/body to 25 g/body.

(III) Method for Measuring Glucose Metabolism Ability

Use of the above-described composition for measuring glucose metabolism ability of the present invention allows measurement of glucose metabolism ability in a subject (a human, or a mammal other than humans).

As described below, the measurement of glucose metabolism ability can basically be performed through the step of administering the above composition, which comprises the labeled C-glucose as an active ingredient, to a mammal, including a human (subject), and collecting expired air ([step (a)] of the method of the present invention), and the step of measuring the abundance of carbon dioxide contained in the expired air (the ratio of labeled $CO_2$ amount to unlabeled $CO_2$ amount or the ratio of labeled $CO_2$ amount to total $CO_2$ amount) ([step (b)] of the method of the present invention).

[Step (a)] The step of administering a composition to a subject and collecting expired air, the composition comprising, as an active ingredient, glucose labeled with at least one isotope of C (labeled C-glucose), wherein the glucose is converted in the body into labeled carbon dioxide that is excreted in expired air; and

[Step (b)] The step of determining the ratio of labeled $CO_2$ amount to unlabeled $CO_2$ amount contained in the expired air or the ratio of labeled $CO_2$ amount to total $CO_2$ amount contained in the expired air.

As described above, the labeled C-glucose used in the present invention has a feature such that, after being orally or intravenously administered to a subject, the labeled C-glucose is metabolized according to glucose metabolism ability of the subject and excreted in expired air in the form of "carbon dioxide containing labeled C," which reflects the degree of the glucose metabolism ability.

There is no particular limitation on the method for administering the composition of the present invention, which comprises the labeled C-glucose, as an active ingredient, and the composition may be orally administered or intravenously administered. Oral administration is preferable since it is a non-invasive method, whereas intravenous administration is preferable in terms of high accuracy, as indicated in Experimental Example 4.

The amount of the labeled C-glucose (active ingredient) contained in the composition for measuring glucose metabolism ability of the present invention may be suitably selected according to each case. Whether the composition for measuring glucose metabolism ability is orally administered or intravenously administered, the dose is adjusted so that the amount of the labeled C-glucose (active ingredient) is in the range of 5 mg/body to 50 g/body, and preferably 10 mg/body to 25 g/body.

As described above, the target subjects of the present invention are humans, or mammals other than humans. Examples of mammals other than humans include mice, rats, guinea pigs, rabbits, dogs, cats, monkeys, pigs, cattle, horses, and the like. The mammals other than humans are preferably test animals such as mice, rats, guinea pigs, rabbits, dogs, and monkeys.

The subject may be in a fasting state or non-fasting state before being subjected to step (a). As indicated in Experimental Example 4 described later, when a subject in a glucose-loaded state, rather than a subject in a fasting state, is subjected to step (a), glucose metabolism ability can be measured with high accuracy for a short period of time. Thus, the subject is preferably in a non-fasting state, in particular, a glucose-loaded state. More specifically, it is preferable that a subject in a fasting state is given a saccharide (e.g., glucose), a food or beverage comprising a saccharide, or a food or beverage comprising a component that is metabolized to a saccharide, at least 120 minutes, and more preferably at least 60 minutes before being subjected to step (a), to render the subject in a glucose-loaded state. The dose of the saccharide or food or beverage is adjusted, for example, so that the amount of glucose administered into the body or glucose produced by metabolism in the body is about 450 mg to 2 g/kg.

Here, there is no limitation on the food or beverage comprising a saccharide, or the food or beverage comprising a component that is metabolized to a saccharide. Examples include a liquid, semi-liquid, or solid food or beverage comprising at least one member selected from the group consisting of proteins (including semi-digested proteins), amino acids, fats, electrolytes, trace elements, and vitamins, in addition to a saccharide or a component that is metabolized to a saccharide. Here, examples of saccharides include, but are not limited to, glucose, saccharose(sucrose), maltose, sorbitol, oligosaccharides carbohydrates, and the like. Glucose and maltodextrin are preferable.

There is no limitation on the food or beverage for use in the glucose tolerance test. Specifically, enteral nutrition agents containing saccharides (maltodextrin and sucrose), like "Racol (registered trademark) Liquid for Enteral Use" used in the below-described Experimental Examples, may be used.

The case in which a composition comprising $^{13}C$-labeled glucose as an active ingredient is used (i.e., the case in which the labeled $CO_2$ measured is $^{13}CO_2$) is described below as an example of the method for measuring glucose metabolism ability of a subject based on the abundance of carbon dioxide contained in expired air collected in step (a) (the ratio of labeled $CO_2$ amount to unlabeled $CO_2$ amount or the ratio of labeled $CO_2$ amount to total $CO_2$ amount).

(1) The abundance of carbon dioxide contained in the collected expired air (the ratio of $^{13}CO_2$ amount to total $CO_2$ amount) is calculated according to the below-described method as the amount of change in $^{13}C$ concentration ($\Delta \% \ ^{13}C$), which is obtained by subtracting the $^{13}C$ concentration (atom %) $[(\% \ ^{13}C)_0]$ before administration of $^{13}C$-labeled glucose.

More specifically, the $^{13}C$ concentration (atom %) in total carbon contained in expired air collected t hr. after administration of the reagent [$^{13}C$ concentration (% $^{13}C$) in expired air] [$(\% \ ^{13}C)_t$] is determined; further, the $^{13}C$ concentration (atom %) before administration of the $^{13}C$-labeled compound [$(\% \ ^{13}C)_0$] is subtracted from the $(\% \ ^{13}C)_t$ according to Formula 6, thereby obtaining the amount of change in the $^{13}C$ concentration ($\Delta \% \ ^{13}C$).

$$^{13}C \text{ concentration (atom \%)} = [^{13}C/(^{13}C+^{12}C)] \times 100$$

$$\Delta \% \ ^{13}C = (\% \ ^{13}C)_t - (\% \ ^{13}C)_0 \quad \text{(Formula 6)}$$

$\Delta \% \ ^{13}C$: amount of change in $^{13}C$ concentration (atom %)
$(\% \ ^{13}C)_t$: $^{13}C$ concentration t hr. after reagent administration (atom %)
$(\% \ ^{13}C)_0$: $^{13}C$ concentration 0 hr. before reagent administration (atom %)

(2) If necessary, the amount of change in the $^{13}C$ concentration ($\Delta \% \ ^{13}C$) may be converted into $\Delta^{13}C$ value (‰) [amount of change in $\delta^{13}C$ value (‰) or DOB (‰)] based on Formula 5 and Formula 3.

$$\% \ ^{13}C = \{[(\delta^{13}C/1000)+1] \times R_{PDB} \times 100\} / \{[[(\delta^{13}C/1000)+1] \times R_{PDB}]+1\} \quad \text{(Formula 5)}$$

% $^{13}C$: $^{13}C$ concentration (atom %)
$\delta^{13}C$: $\delta^{13}C$ value (‰)
$R_{PDB}$: abundance of $^{13}C$ in PDB standard gas=0.0112372

$$\Delta^{13}C(‰) = (\delta^{13}C)_t - (\delta^{13}C)_0 \quad \text{(Formula 3)}$$

$\Delta^{13}C(‰)$: amount of change in $\delta^{13}C$ value (‰)
$(\delta^{13}C)_t$: $\delta^{13}C$ value t hr. after reagent administration (‰)
$(\delta^{13}C)_0$: $\delta^{13}C$ value 0 hr. before reagent administration (‰)

The concentration of labeled C excreted in expired air after the composition for measuring glucose metabolism ability, which comprises the labeled C-glucose as an active ingredient, is administered, or the corresponding $\Delta \% \ ^{13}C$ (atom %) or $\Delta^{13}C$ value (‰) reflect glucose metabolism ability of a subject, as indicated in the Experimental Examples described later. The method of the present invention, which uses the composition, allows glucose metabolism ability of the subject, to be measured rapidly and with high accuracy.

The measurement and analysis of the labeled carbon dioxide contained in expired air vary depending on whether the isotope used is radioactive or non-radioactive. However, the measurement and analysis may be performed by a commonly used analysis method, such as the liquid scintillation counter method, mass spectrometry, infrared spectroscopy, emission spectrometry, or the magnetic resonance spectrum method. From the viewpoint of measurement accuracy, infrared spectroscopy and mass spectrometry are preferable.

Glucose metabolism ability of a subject can be determined by the following method, using, as an index, "the ratio of labeled COP amount to unlabeled $CO_2$ amount contained in the expired air or the ratio of labeled $CO_2$ amount to total $CO_2$ amount contained in the expired air" ($\Delta \% \ ^{13}C$ (atom %) or $\Delta^{13}C$ value (‰)) obtained in step (b) described above.

(c-1) "The ratio of labeled $CO_2$ amount to unlabeled $CO_2$ amount contained in the expired air or the ratio of labeled $CO_2$ amount to total $CO_2$ amount contained in the expired air" ($\Delta \% \ ^{13}C$ (atom %) or $\Delta^{13}C$ value (‰)) obtained in the subject in step (b) (subject value) is compared with "the corresponding ratio of labeled $CO_2$ amount to unlabeled $CO_2$ amount contained in the expired air or the corresponding ratio of labeled $CO_2$ amount to total $CO_2$ amount contained in the expired air" (Δ % $^{13}$C (atom %) or $\Delta^{13}$C value (‰)) of a healthy subject (control value).

(c-2) As a result of the comparison, when the subject value is lower than the control value, it is determined that the glucose metabolism ability of the former subject is decreased. If the subject value is higher than the control value, it is determined that the glucose metabolism ability of the former subject is enhanced.

Here, the healthy subject means a subject that is healthy with regard to diabetes, i.e., a subject in which diabetes has not developed, and that is not in a stage before onset of diabetes (non-diabetic subject).

As indicated in Experimental Example 2 (FIG. 2), it is shown that glucose metabolism ability of patients in whom diabetes has developed is lower than glucose metabolism ability of healthy subjects, and that as the symptoms of diabetes progress and the severity increases, glucose metabolism ability notably decreases. On the other hand, it is shown that glucose metabolism ability of subjects in which diabetes has not yet developed, but that are in a stage before onset of diabetes, is higher than glucose metabolism ability of healthy subjects. Thus, as described in detail in (IV) below, by measuring glucose metabolism ability of a subject by the method of the present invention, not only can a stage after onset of diabetes be evaluated and determined, but a subject in a stage before onset of diabetes can also be detected. More specifically, it is determined in the method of the present invention that diabetes has developed in a subject whose glucose metabolism ability is lower than that of a healthy subject, whereas it is determined in the method of the present invention that a subject whose glucose metabolism ability is higher than that of a healthy subject is in a stage before onset of diabetes. This is, since the method for measuring glucose metabolism ability of the present invention can detect a subject that is in a stage before onset of diabetes, it can determine the risk of onset of diabetes, thus contributing to the prevention of onset of diabetes.

As described above, the stage (severity) of a diabetic patient in whom diabetes has already developed can be determined and monitored by measuring glucose metabolism ability of the diabetic patient. Likewise, as indicated in Experimental Examples 5 and 6 (FIGS. 12 and 13), the effect of treatment for diabetes on a diabetic patient receiving the treatment for diabetes can also be determined and monitored by measuring glucose metabolism ability of the diabetic patient. The details are described in (V) below.

This determination and monitoring may be performed by a method of diagnosis of diabetes known or commonly used in this field (such as measurement of blood glucose level, insulin resistance test, and measurement of HbA1c) in parallel with the method of the present invention, which uses a breath test.

(IV) Method for Determining a Stage before Onset of Diabetes or/and a Stage after Onset of Diabetes As described above, a stage before onset of diabetes or/and a stage after onset of diabetes in a subject can be determined by using, as an index, glucose metabolism ability of the subject obtained by the method for measuring glucose metabolism ability of the present invention.

More specifically, the diabetes stage can be determined based on the results obtained in step (c) in the following steps (a) to (c) by determining that a subject whose glucose metabolism ability is determined to be decreased compared with glucose metabolism ability of a healthy subject is a diabetic patient (patient in whom diabetes has developed), and that a subject whose glucose metabolism ability is determined to be enhanced (increased) compared with glucose metabolism ability of a healthy subject is a patient in a stage before onset of diabetes (diabetes pre-onset stage patient).

[Step (a)] The step of administering a composition to a subject and collecting expired air, the composition comprising, as an active ingredient, glucose labeled with at least one isotope of C (labeled C-glucose), wherein the glucose is converted in the body into labeled carbon dioxide that is excreted in expired air;

[Step (b)] The step of determining the ratio of labeled $CO_2$ amount to unlabeled $CO_2$ amount contained in the expired air or the ratio of labeled $CO_2$ amount to total $CO_2$ amount contained in the expired air; and

[Step (c)] The step of comparing "the ratio of labeled $CO_2$ amount to unlabeled $CO_2$ amount contained in the expired air or the ratio of labeled $CO_2$ amount to total $CO_2$ amount contained in the expired air" (Δ % $^{13}$C (atom %) or $\Delta^{13}$C value (‰)) obtained in the subject in step (b) (subject value) with "the corresponding ratio of labeled $CO_2$ amount to unlabeled $CO_2$ amount contained in the expired air or the corresponding ratio of labeled $CO_2$ amount to total $CO_2$ amount contained in the expired air" (Δ % $^{13}$C (atom %) or $\Delta^{13}$C value (‰) of a healthy subject (control value), and determining that glucose metabolism ability of the former subject is decreased when the subject value is lower than the control value, and that glucose metabolism ability of the former subject is enhanced when the subject value is higher than the control value.

In the "method for determining a stage before onset of diabetes or/and a stage after onset of diabetes" of the present invention, the above-mentioned [Step (c)] can be restated as follows.

[Step (c')] The step of comparing "the ratio of labeled $CO_2$ amount to unlabeled $CO_2$ amount contained in the expired air or the ratio of labeled $CO_2$ amount to total $CO_2$ amount contained in the expired air" (Δ % $^{13}$C (atom %) or $\Delta^{13}$C value (‰)) obtained in the subject in step (b) (subject value) with "the corresponding ratio of labeled $CO_2$ amount to unlabeled $CO_2$ amount contained in the expired air or the corresponding ratio of labeled $CO_2$ amount to total $CO_2$ amount contained in the expired air" (Δ % $^{13}$C (atom %) or $\Delta^{13}$C value (‰)) of a healthy subject (control value), and determining that diabetes has developed in the former subject when the subject value is lower than the control value, and that the former subject is in a stage before onset of diabetes when the subject value is higher than the control value.

In particular, the method of the present invention is useful in that patients in a stage before onset of diabetes (diabetes pre-onset stage patients), who are difficult to identify by hitherto known methods, can be distinguished from healthy subjects. As indicated in Experimental Example 2 (FIG. 2) the larger the degree of decrease in glucose metabolism ability, the larger the degree of progression of diabetes (severity); there is a correlation between the degree of decrease in glucose metabolism ability and the degree of progression of diabetes (severity). Thus, the method of the present invention makes it possible to measure and evaluate, as well as monitor the degree of progression of diabetes (severity) based on the degree of decrease in glucose metabolism ability.

A diabetes stage (stage before onset of diabetes or/and a stage after onset of diabetes) may also be determined by the following method. According to this method, not only diabetic patients, but also patients in a stage before onset of diabetes can be distinguished from healthy subjects more clearly and with high accuracy.

(1) A method for determining a correlation between a [blood glucose level](mg/dl) of a subject under fasting conditions and a parameter obtained by dividing "the ratio of labeled $CO_2$ amount to unlabeled $CO_2$ amount contained in the expired air or the ratio of labeled $CO_2$ amount to total $CO_2$ amount, contained in the expired air" ($\Delta$ % $^{13}$C(atom %) or $\Delta^{13}$C value (‰)) at least one point in time after the labeled C-glucose is administered to the subject; preferably within 120 minutes after administration of the labeled C-glucose by a blood insulin concentration (ng/mL) of the subject under fasting conditions (for example, [$\Delta^{13}$C(‰)$_{(t\ minutes)}$/insulin (mL/ng)] (‰·mL/ng))).

More specifically, as indicated in Experimental Example 2 (3-3) (FIG. 4), diabetic patients and patients in a stage before onset of diabetes can be distinguished from healthy subjects by plotting the parameter (for example, [$\Delta^{13}$C(‰)$_{(t)}$/insulin] (‰·mL/ng) (t=10 minutes) and the [blood glucose level] (mg/dl) in a graph in which the ordinate represents the parameter and the abscissa represents the blood glucose level, and examining the correlation between the parameter and the blood glucose level.

Figure 4:
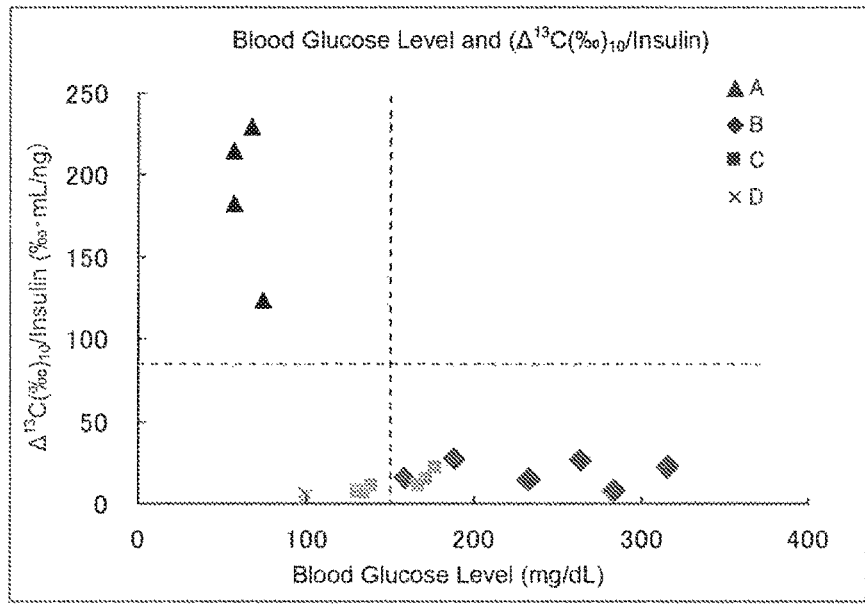
FIG. 4 illustrates the results of Experimental Example 2.

As shown in FIG. 4, when the blood glucose level represented by the abscissa is divided at, for example, 150 mg/dl and the [$\Delta^{13}$C(‰)$_{(t)}$/insulin] (t=10 minutes) represented by the ordinate is divided at, for example, 90‰·mL/ng, the healthy group concentrates in the upper-left section (blood glucose level of 150 mg/dl or less, [$\Delta^{13}$C(‰)$_{(T)}$/insulin] of 90‰·mL/ng or more), whereas the diabetic patients and the patients in a stage before onset of diabetes concentrate in the area in which the [$\Delta^{13}$C(‰)$_{(t)}$/insulin] is 90‰·mL/ng or less, particularly in lower values. In particular, the patients in a stage before onset of diabetes concentrate in the area in which the [$\Delta^{13}$C(‰)$_{(t)}$/insulin] is 90‰·mL/ng or less and the blood glucose level is 150 mg/dl or less. Further, as diabetes progresses after onset (the severity increases), plot points tend to shift to the right side (area in which the blood glucose level is higher than 150 mg/dl) of FIG. 4 in accordance with the degree of progression.

(2) A method for determining a correlation between a [blood glucose level](mg/dl) of a subject under fasting conditions and a parameter obtained by dividing the area under the curve of "the ratio of labeled $CO_2$ amount to unlabeled $CO_2$ amount contained in the expired air or the ratio of labeled $CO_2$ amount to total $CO_2$ amount contained in the expired air" ($\Delta$ % $^{13}$C(atom %) or $\Delta^{13}$C value (‰)) obtained within 120 minutes after the labeled C-glucose is administered to the subject by a blood insulin concentration (ng/mL) of the subject under fasting conditions (for example, [$\Delta^{13}$C(‰)AUC$_{(t\ minutes)}$/insulin (mL/ng)] (‰·min·mL/ng)).

More specifically, as indicated in Experimental Example 2 (3-2) (FIG. 3), diabetic patients and patients in a stage before onset of diabetes can be distinguished from healthy subjects by plotting the parameter (for example, [$\Delta^{13}$C(‰) AUC$_t$/insulin] (‰·min·mL/ng), t=120 minutes)) and the [blood glucose level] (mg/dl) in a graph in which the ordinate represents the parameter and the abscissa represents the blood glucose level, and examining the correlation between the parameter and the blood glucose level.

Figure 3:
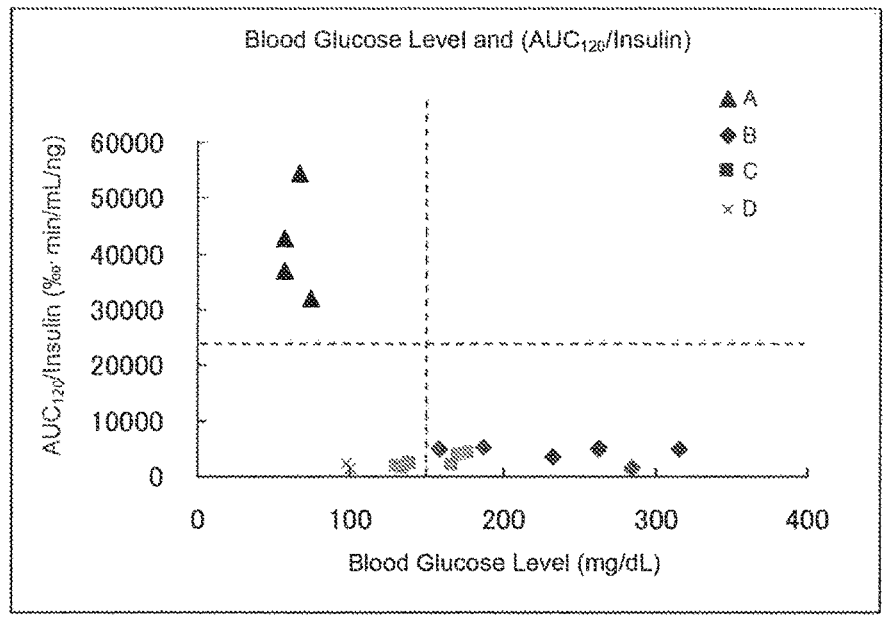
FIG. 3 illustrates the results of Experimental Example 2.

As shown in FIG. 3, when the blood glucose level represented by the abscissa is divided at, for example, 150 mg/dl and the [$\Delta^{13}$C(‰) AUC$_t$/insulin] (t=120 minutes) represented by the ordinate is divided at, for example, 23000‰·min·mL/ng, the healthy group concentrates in the upper-left section (blood glucose level of 150 mg/dl or less, [$\Delta^{13}$C(‰) AUC$_t$/insulin] of 23000‰·min·mL/ng or more), whereas the diabetic patients and patients in a stage before onset of diabetes concentrate in the area in which the [$\Delta^{13}$C(‰) AUC$_t$/insulin] is 23000‰·min·mL/ng or less, particularly in lower levels. In particular, the patients in a stage before onset of diabetes concentrate in the area in which the [$\Delta^{13}$C(‰)AUC$_t$/insulin] is 23000‰·min·mL/ng or less and the blood glucose level is 150 mg/dl or less. Further, as diabetes progresses after onset, (as the severity increases), plot points tend to shift to the right side (area in which the blood glucose level is higher than 150 mg/dl) of FIG. 3 in accordance with the degree of progression.

As described above, the method of the present invention makes it possible to defect subjects in a stage before onset of diabetes distinctively from healthy subjects and diabetic patients with a quick test. Therefore, suppression or prevention of onset of diabetes can be expected by giving feedback of the results to subjects in a stage before onset of diabetes and taking appropriate measures. In addition, the presence or absence or degree of progression of onset of diabetes, or the severity in diabetic patients can be managed and observed over time by monitoring subjects over time.

(IV) Method for Detecting the Effect of Treatment for Diabetes on a Diabetic Patient As described above, the effect of treatment for diabetes on a subject receiving the treatment for diabetes (diabetic patient) can foe detected and evaluated by using, as an index, glucose metabolism ability of the subject obtained by the method for measuring glucose metabolism ability of the present invention.

More specifically, a subject is subjected to steps (a') and (b) below before and after treatment for diabetes; "the ratio of labeled $CO_2$ amount to unlabeled $CO_2$ amount, contained in the expired air or the ratio of labeled $CO_2$ amount to total $CO_2$ amount contained in the expired air" ($\Delta$ % $^{13}$C (atom %) or $\Delta^{13}$C value (‰)) obtained before and after the treatment for diabetes is compared; and it can be determined that the treatment for diabetes is effective when the value obtained after the treatment for diabetes is higher than the value obtained before the treatment for diabetes.

[Step (a')] The step of administering a composition to a subject before and after treatment for diabetes and collecting expired air, the composition comprising, as active ingredient, glucose labeled with at least one isotope of C (labeled C-glucose), wherein the glucose is converted in the body into labeled carbon dioxide that is excreted in expired air;

[Step (b)] The step of determining the ratio of labeled $CO_2$ amount to unlabeled $CO_2$ amount contained in the expired air before and after the treatment for diabetes or the ratio of labeled $CO_2$ amount to total $CO_2$ amount contained in the expired air before and after the treatment for diabetes; and

[Step (d)] The step of comparing "the ratio of labeled $CO_2$ amount to unlabeled $CO_2$ amount contained in the expired air or the ratio of labeled $CO_2$ amount to total $CO_2$ amount contained in the expired air" ($\Delta$ % $^{13}$C (atom %) or $\Delta^{13}$C value (‰)) obtained in the subject after the treatment for diabetes in step (b) (subject value) with "the corresponding ratio of labeled $CO_2$ amount to unlabeled $CO_2$ amount contained in the expired air or the corresponding ratio of labeled $CO_2$ amount to total $CO_2$ amount contained in the expired air" ($\Delta$ % $^{13}$C (atom %) or $\Delta^{13}$C value (‰)) obtained in the subject before the treatment for diabetes in step (b) (control value), and determining that the treatment for diabetes is effective in the subject when the subject value is higher than the control value, and that the treatment for diabetes is not effective in the subject when the subject value is the same as or lower than the control value.

According to the method of the present invention, the effect of treatment for diabetes can be measured and evaluated, and monitored by using, as an index, an increase in glucose metabolism ability of a diabetic patient receiving the treatment for diabetes.

EXAMPLES

Examples and Experimental Examples are described below to further clarify the present invention. However, the present invention is not limited to these Examples.

Experimental Example 1

Difference in $^{13}C$-labeled Positions of Glucose
(1) Preparation of $^{13}$-glucose Solutions
(a) 1-$^{13}C$-glucose (glucose in which the carbon atom at the 1-position is replaced by $^{13}C$; MW: 181, produced by Cambridge Isotope Laboratory) was prepared in physiological saline so that the concentration became 300 μmol/mL.
(b) 2-$^{13}C$-glucose (glucose in which the carbon atom at the 2-position is replaced by $^{13}C$; MW: 181, produced by Cambridge Isotope Laboratory) was prepared in physiological saline so that the concentration became 300 μmol/mL.
(c) 3-$^{13}C$-glucose (glucose in which the carbon atom at the 3-position is replaced by $^{13}C$; MW: 181, produced by Cambridge Isotope Laboratory) was prepared in physiological saline so that the concentration became 300 μmol/mL.
(d) U-$^{13}C$-glucose (glucose in which all of the carbon atoms are replaced by $^{13}C$; MW: 186, produced by Cambridge Isotope Laboratory) was prepared in physiological saline so that the concentration became 50 μmol/mL.
(2) Experimental Method
Fasted rats (male, SD rats) as experimental animals were divided into four groups (n=4 per group). The above-prepared $^{13}C$-glucose solutions were individually intravenously administered to the rats in each group (1-$^{13}$-Glc-administration group, 2-$^{13}C$-Glc-administration group, 3-$^{13}C$-Glc-administration group, and U-$^{13}$-Glc-adrainistration group) in an amount of 1 mL/kg. Expired air was collected before the administration of each $^{13}C$-glucose solution (0 minutes) and at each point in time (10, 20, 30, 40, 50, 60, 80, 100, and 120 minutes) after the administration of each $^{13}C$-glucose solution, $\Delta^{13}C(‰)$ was determined with a mass spectrometer for expired air analysis (ABCA: produced by Sercon) from the concentration of $^{13}CO_2$ excreted in the expired air.

The $\Delta^{13}C(‰)$ was determined by measuring the $^{13}CO_2/^{12}CO_2$ concentration ratio ($\delta^{13}C$ value) in the expired air before the administration of each $^{13}C$-glucose solution (0 minutes) and in the expired air at each point in time for collecting the expired air (t minutes) after the administration of each $^{13}C$-glucose solution, and calculating $\Delta^{13}C(‰)$ from the difference between the $\delta^{13}C$ value ($\delta^{13}C_t$) at each collection point in time (t) and the $\delta^{13}C$ value ($\delta^{13}C_0$) before the administration ($\delta^{13}C_t-\delta^{13}C_0$) (the same applies to the below-described Experimental Examples).
(3) Experimental Results
FIG. 1 shows changes in the $\Delta^{13}C(‰)$ in the expired air measured after the $^{13}C$-glucose solutions were individually administered to each of the four groups of rats. In FIG. 1, the $\Delta^{13}C(‰)$ in the expired air is plotted on the ordinate, and the expired air collection time (minutes) (t minutes) after the administration of each $^{13}C$-glucose solution is plotted on the abscissa.

As shown in FIG. 1, the highest $\Delta^{13}C(‰)$ up to 30 minutes after the glucose solution administration was observed in the 3-$^{13}C$-Glc-administration group (-▲-), followed by the U-$^{13}C$-Glc-administration group (-×-). This result reveals that among 1-$^{13}C$-glucose, 2-$^{13}C$-glucose, 3-$^{13}C$-glucose, and U-$^{13}C$-glucose, the $^{13}C$-glucose that is excreted in expired air in the form of $^{13}CO_2$ more rapidly after being administered to the body and is reflected in the $\Delta^{13}C(‰)$ value is 3-$^{13}C$-glucose, followed by U-$^{13}C$-glucose. Specifically, the $^{13}C$-glucose that enables the $\Delta^{13}C(‰)$ value to be measured for a short period of time is preferably 3-$^{13}C$-glucose and U-$^{13}C$-glucose.

Experimental Example 2

Monitoring of a Diabetes Stage with a Breath Test (I)
(1) Preparation of U-$^{13}C$-glucose Solution for Oral Administration
A U-$^{13}C$-glucose solution for oral administration at a concentration of 50 μmol/4 mL was prepared by dissolving U-$^{13}C$-glucose (MW: 186, produced by Cambridge Isotope Laboratory) in physiological saline.
(2) Stage Monitoring Experiment
The rats of the total four groups A to D shown in Table 1 (male, ZDF rats (Lean or Fatty), n=4 to 6 per group) were used as experimental animals. After the rats of each group were fasted, the above-prepared U-$^{13}C$-glucose solution for oral administration was forcibly administered orally in an amount of 4 mL/kg.

TABLE 1

| | Lean or Fatty | Number of Rats (n) | Blood Glucose Level under Fasting Conditions (mg/dL) | Blood Insulin Concentration under Fasting Conditions (ng/mL) |
|---|---|---|---|---|
| Group A: Healthy Group | Lean | 4 | 63.8 | 0.21 |
| Group B: Diabetes Severe Onset Group | Fatty | 6 | 240.3 | 1.97 |
| Group C: Diabetes Moderate Onset Group | Fatty | 6 | 153.7 | 4.10 |
| Group D: Diabetes Pre-Onset Stage Group | Fatty | 4 | 99.0 | 5.91 |

Figure 2:
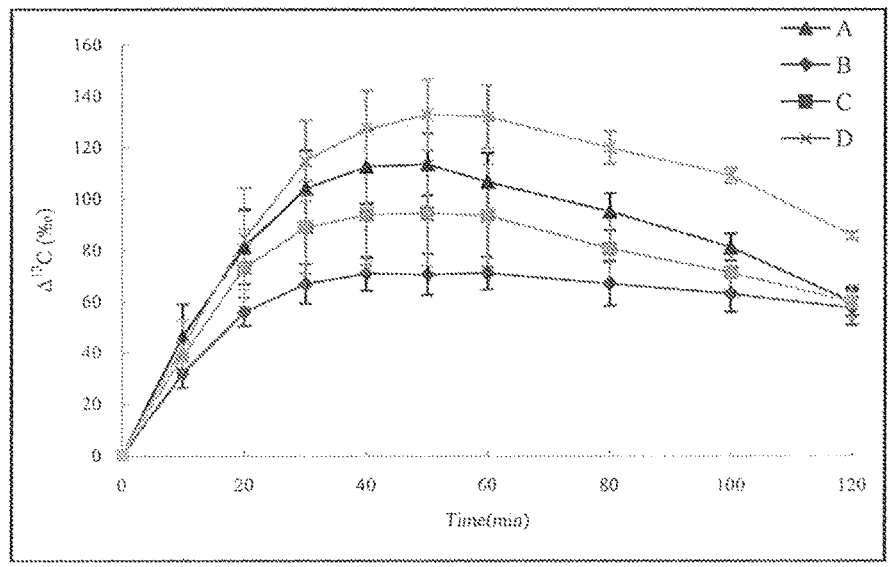
FIG. 2 illustrates the results of Experimental Example 2.

Expired air was collected before the administration of the U-$^{13}C$-glucose solution for oral administration (0 minutes), and at each point in time (10, 20, 30, 40, 50, 60, 80, 100, and 120 minutes) after the administration of the U-$^{13}$-glucose solution for oral administration. $\Delta^{13}C(‰)$ was determined with a mass spectrometer for expired air analysis (ABCA: produced by Sercon) from the concentration of $^{13}CO_2$ excreted in the expired air.
(3) Experimental Results
(3-1) FIG. 2 shows changes in the $\Delta^{13}C(‰)$ in the expired air measured after the U-$^{13}C$-glucose solution for oral administration was administered to the four groups of rats. In FIG. 2, the $\Delta^{13}C(‰)$ in the expired air is plotted on the ordinate, and the expired air collection time (minutes) after the administration of the U-$^{13}$C-glucose solution for oral administration is plotted on the abscissa.

As shown in FIG. 2, the $\Delta^{13}$C(‰) values of the diabetes moderate onset group (Group C: -■-) and the diabetes severe onset group (Group B: -♦-) were lower than that of the healthy group (Group A: -▲-). On the other hand, the $\Delta^{13}$C(‰) value of the diabetes pre-onset stage group (Group D: -×-) was higher than those of the healthy group and the diabetes onset groups (diabetes moderate onset group and diabetes severe onset group).

This reveals that in a stage before onset of diabetes, glucose metabolism ability is enhanced compared with that in the healthy state, and U-$^{13}$C-glucose is more rapidly metabolized and excreted in expired air in the form of $^{13}CO_2$. It is also revealed that once diabetes develops, glucose metabolism ability decreases to reduce glucose metabolism, resulting in decrease in the amount of $^{13}CO_2$ excreted in expired air after $^{13}$C-glucose is metabolized; it is further revealed that the decrease in glucose metabolism ability (decrease in $^{13}CO_2$ excretion amount) correlates with severity of diabetes.

This result indicates that not only a stage after onset of diabetes, but also a stage before onset of diabetes can be determined by using $^{13}$C-glucose as a test substance, and measuring glucose metabolism ability with a breath test.

(3-2) FIG. 3 shows the correlation between each "blood glucose level (mg/dL)" of the four groups of rats and each value obtained by dividing the [area under the $\Delta^{13}$C(‰)-expired air collection time (120 minutes) curve (AUC)] of each group by the insulin concentration (mg/dL) of each group ("AUC$_{120}$/insulin (‰·min·mL/ng)"). In FIG. 3, the AUC$_{120}$/insulin concentration (‰·min·mL/ng) is plotted on the ordinate, whereas the blood glucose level (mg/dL) is plotted on the abscissa.

As shown in FIG. 3, the AUC$_{(120\ minutes)}$ with respect to insulin concentration [AUC$_{120}$/insulin(‰·min·mL/ng)] was significantly low in the diabetes pre-onset stage group (Group D: -×-) as well as in the diabetes onset groups, i.e., the diabetes moderate onset group (Group C: -■-) and the diabetes severe onset group (Group B: -♦-). These values were clearly different from that of the healthy group (Group A: -▲-). Further, FIG. 3 shows that as the diabetes stage progresses, plot points shift to the right side with increase in blood glucose level. This confirms that determining the correlation between the parameter [AUC$_{120}$/insulin (‰·min·mL/ng)] and the [blood glucose level (mg/dL)] makes it possible to not only distinguish a stage before onset of diabetes and diabetes from a healthy stage, but also determine and monitor a stage before onset of diabetes and a stage of diabetes (these are collectively referred to as "diabetes stage"). The diabetes stage determination using this parameter is useful in diagnosis of, in particular, a stage before onset of diabetes, which is difficult to distinguish by hitherto known methods.

(3-3) FIG. 4 show the correlation between each value obtained by dividing the $\Delta^{13}$C(‰) of the four groups of rats 10 minutes after the oral administration of the U-$^{13}$C-glucose by the insulin concentration (ng/mL) of each group "$\Delta^{13}$C(‰)$_{(10\ minutes)}$/insulin (‰·mL/ng)" and the "blood glucose level (mg/dL)" of each group. In FIG. 4, the "$\Delta^{13}$C(‰)$_{(10\ minutes)}$/insulin concentration" (‰·mL/ng) is plotted on the ordinate, whereas the blood glucose level (mg/dL) is plotted on the abscissa.

This result confirms that even if the "$\Delta^{13}$C(‰)$_{(10\ minutes)}$/insulin (‰·mL/ng)" is plotted on the ordinate in FIG. 3 described above in place of the "AUC$_{120}$/insulin (‰·min·mL/ng)," a stage before onset of diabetes and diabetes can be distinguished from a healthy state, and a diabetes stage can be determined and monitored. Specifically, determining the correlation between the [blood glucose level] (mg/dl) and the parameter obtained by dividing the $\Delta^{13}$C(‰) at a point in time after $^{13}$C-glucose administration (t minutes after administration) ($\Delta^{13}$C(‰)$_{(t\ minutes)}$ by insulin concentration [$\Delta^{13}$C(‰)$_{(t\ minutes)}$/insulin] (‰·mL/ng) makes it possible to not only distinguish a stage before onset of diabetes and diabetes from a healthy state, but also determine and monitor a stage before onset of diabetes and a stage of diabetes (diabetes stage). The above point in time (t minutes) for measurement may be any point in time, as long as it is a point in time after $^{13}$C-glucose administration, From the viewpoint of utilizing an advantage of the present invention, i.e., performing the above distinction or determination in a short period of time, the point in time is within 120 minutes, preferably within 60 minutes, and more preferably within 30 minutes after $^{13}$C-glucose administration. The point in time is preferably, but not limited to, at least 10 minutes after $^{13}$C-glucose administration.

The diabetes stage determination using this parameter is useful in diagnosis of, in particular, a stage before onset of diabetes, which is difficult to distinguish in a short period of time by hitherto known methods.

Experimental Example 3

Monitoring of a Diabetes Stage with a Breath Test (II)

(1) Preparation of a U-$^{13}$C-glucose Solution for Oral Administration

A U-$^{13}$C-glucose solution for oral administration at a concentration of 50 μmol/4 mL was prepared by dissolving U-$^{13}$C-glucose (MW: 186, produced by Cambridge Isotope Laboratory) in physiological saline.

(2) Experiment for Monitoring a Stage in Change in Weeks of Age

Fasted ZDF lean rats (non-diabetic rats: healthy group) (male, n=4) use fasted ZDF Fatty rats (male, n=4) were used as experimental animals. The above-prepared solution was forcibly administered orally to the ZDF Fatty rats at 9, 10, 13, and 23 weeks of age and to the ZDF Lean rats at 13 weeks of age in an amount of 4 ml/kg. Expired air was collected in each group before the administration of the U-$^{13}$C-glucose solution for oral administration (0 minutes) and at each point in time (10, 20, 30, 40, 50, 60, 80, 100, and 120 minutes) after the adxainistratron of the U-$^{13}$C-glucose solution for oral administration. $\Delta^{13}$C(‰) was determined with a mass spectrometer for expired air analysis (ABCA: produced by Sercon) from the concentration of $^{13}CO_2$ excreted in the expired air.

(3) Experimental Results

Figure 5:
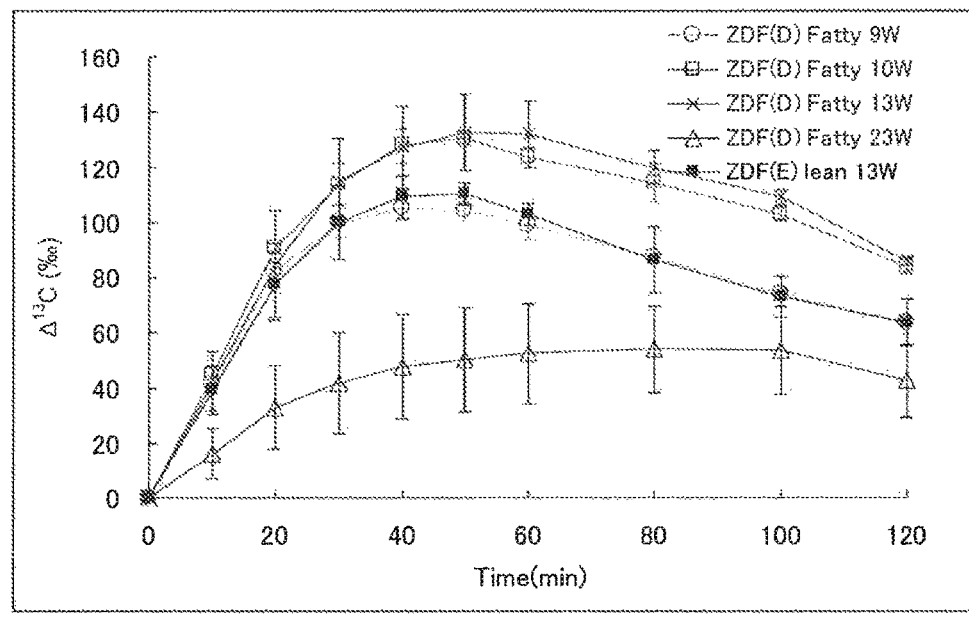
FIG. 5 illustrates the results of Experimental Example 3.

FIG. 5 show changes in the $\Delta^{13}$C(‰) in the expired air measured after the U-$^{13}$C-glucose solution for oral adxainistration was administered at different weeks of age (ZDF Fatty: 9 W, 10 W, 13 W, 23 W; ZDF Lean: 13 W). In FIG. 5, the $\Delta^{13}$C(‰) in the expired air is plotted on the ordinate, whereas the expired air collection time (minutes) after the administration of the U-$^{13}$C-glucose solution for oral administration is plotted on the abscissa.

As shown in FIG. 5, the SDF Fatty rats at 9 weeks of age (-○-) exhibited an expired, air pattern (change in the $\Delta^{13}$C (‰) in the expired air) similar to that of the healthy group (ZDF Lean rats at 13 weeks of age,-■-). On the other hand, glucose metabolism was enhanced in the ZDF Fatty rat group at 10 weeks of age (-□-) and the ZDF Fatty rat group at 13 weeks of age (-×-), and their expired air patterns (changes in the $\Delta^{13}C$(‰) in the expired air) were higher than that of the healthy group (-■-). Further, diabetes developed in the ZDF Fatty rats at 23 weeks of age (-Δ-), and their expired air patterns were lower than that of the healthy group (-■-). This reveals that use of the $\Delta^{13}C$(‰) in the expired air as an index in the breath test using $^{13}C$-glucose makes it possible to not only distinguish a healthy state, a stage before onset of diabetes, and diabetes, but also monitor changes in a stage before onset of diabetes and a stage of diabetes (diabetes stage) over time.

Experimental Example 4

Breath Test Under Glucose-loaded Conditions
(1) Experimental Animals

Figure 6:
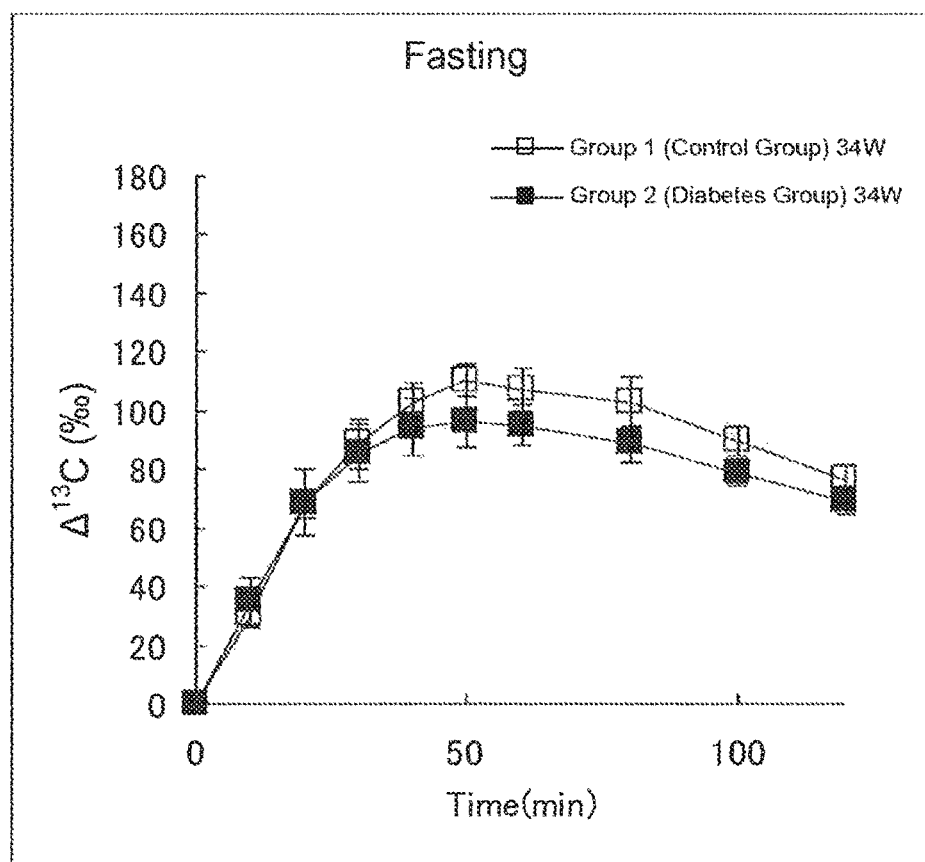
FIG. 6 illustrates the results of Experimental Example 4 (2-1).
Figure 7:
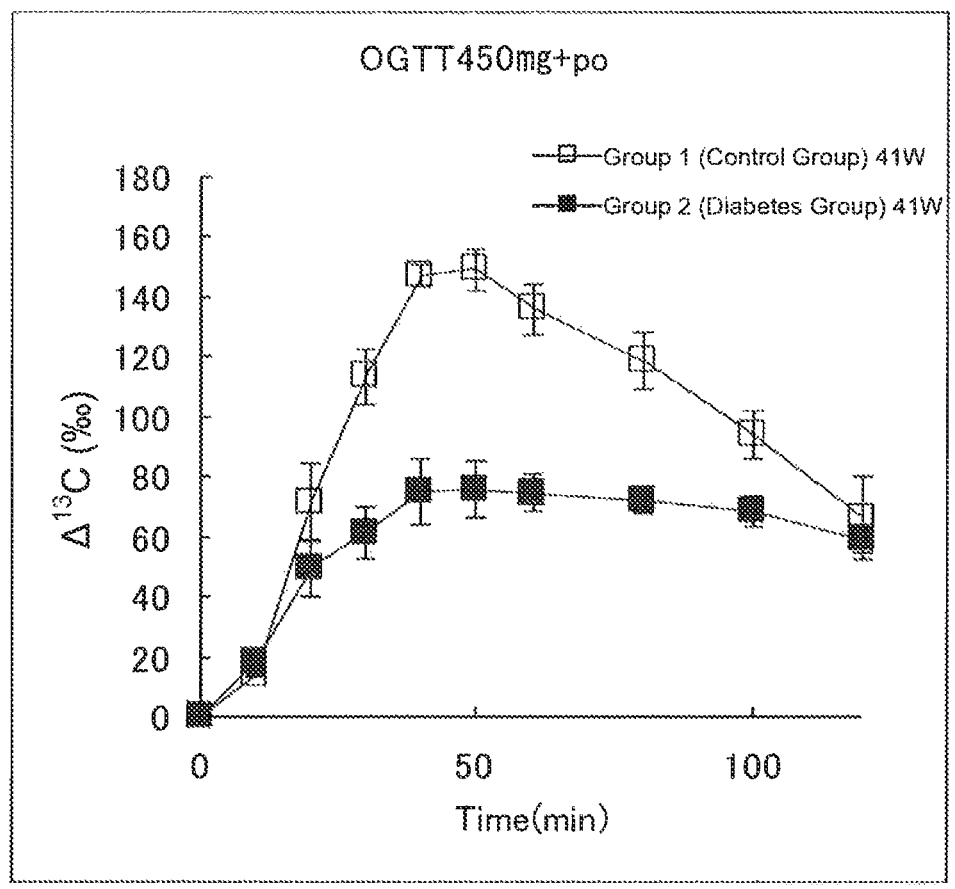
FIG. 7 illustrates the results of Experimental Example 4 (2-2-1).
Figure 8:
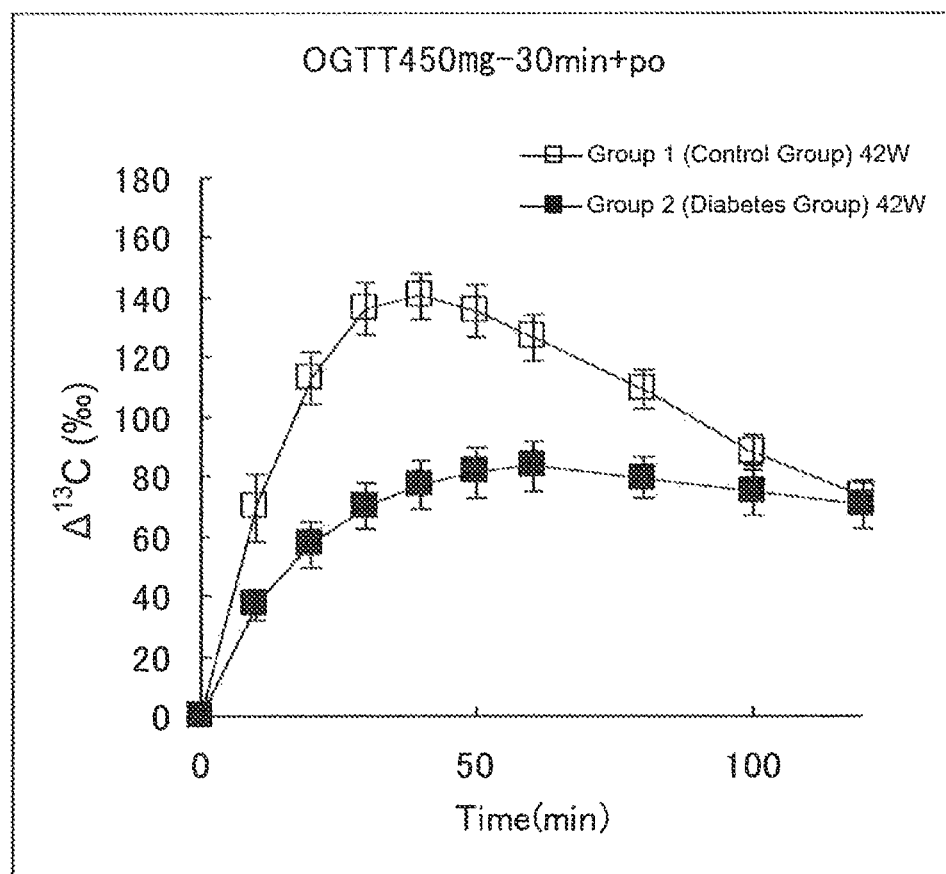
FIG. 8 illustrates the results of Experimental Example 4 (2-2-2).
Figure 9:
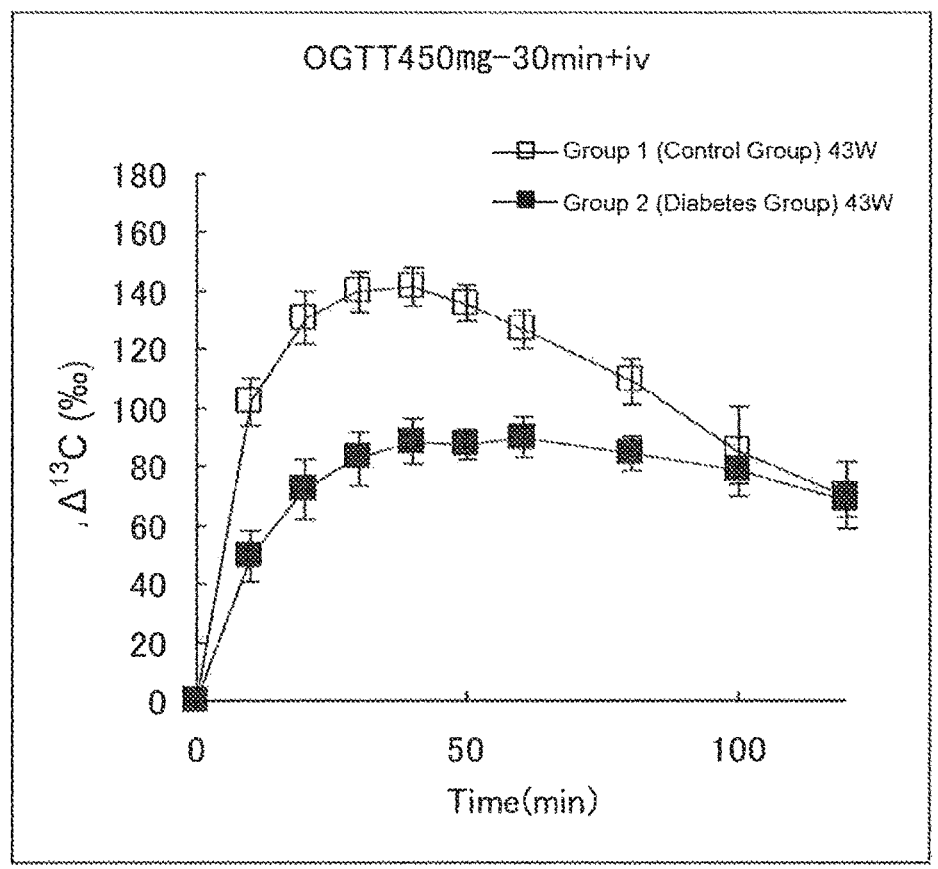
FIG. 9 illustrates the results of Experimental Example 4 (2-2-3).
Figure 10:
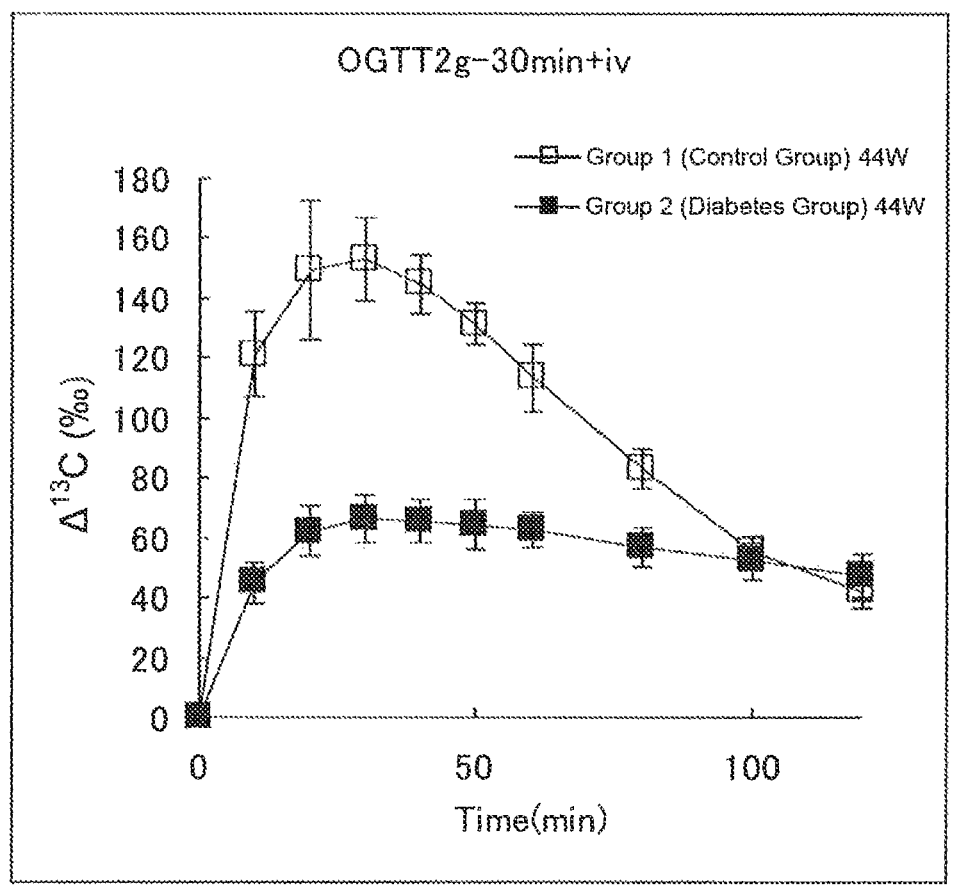
FIG. 10 illustrates the results of Experimental Example 4 (2-2-4).
Figure 11:
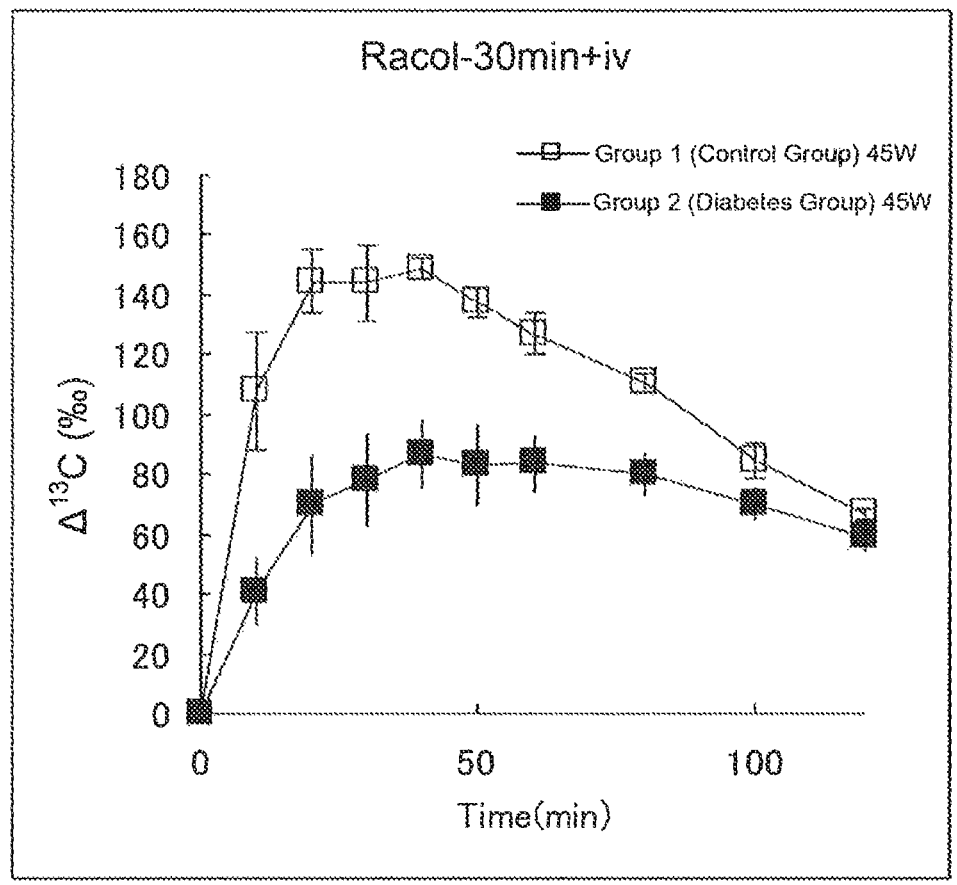
FIG. 11 illustrates the results of Experimental Example 4 (2-2-5).

OLETF rats, which are diabetic animal models, were used as experimental animals, and LETO rats were used as a control. More specifically, after being fasted for 20 hours, Group 1 (control group: OLETF rats, male, n=5) and Group 2 (diabetes group; OLETF rats, male, n=6) were subjected to the following test.
(2) Experimental Method and Results
(2-1) Expired Air Pattern (Change in $\Delta^{13}C$(‰) in Expired Air) under Fasting Conditions An aqueous U-$^{13}C$-glucose solution (50 μmol/4 mL/kg) was orally administered to Group 1 (control group) and Group 2 (diabetes group) under fasting conditions. In each group, expired air was collected before the U-$^{13}C$-glucose administration (0 minutes) and at each point in time (10, 20, 30, 40, 50, 60, 80, 100, and 120 minutes) after the U-$^{13}C$-glucose administration. $\Delta^{13}C$(‰) was determined with a mass spectrometer for expired air analysis (ABCA: produced by Sercon) from the concentration of $^{13}CO_2$ excreted in the expired air. FIG. 6 shows the expired air patterns (changes in the $\Delta^{13}C$(‰) in the expired air).
(2-2) Expired Air Pattern (Change in $\Delta^{13}C$(‰) in Expired Air) under Administration of Glucose in an Amount of 450 mg/4 mL/kg (Under Glucose Loaded Conditions)
(2-2-1) An aqueous glucose solution (450 mg/4 mL/kg) and an aqueous U-$^{13}C$-glucose solution (50 μmol/4 mL/kg) were orally administered simultaneously to the experimental animals of (1), i.e., Group 1 (control group) and Group 2 (diabetes group). As in (2-1), expired air was collected in each group before the U-$^{13}C$-glucose administration (0 minutes) and at each, point in time (10, 20, 30, 40, 50, 60, 80, 100, and 120 minutes) after the U-$^{13}C$-glucose administration. $\Delta^{13}C$(‰) was determined from the concentration of $^{13}CO_2$ excreted in the expired air. FIG. 7 shows the expired air patterns (changes in the $\Delta^{13}C$(‰) in the expired air).
(2-2-2) An aqueous U-$^{13}C$-glucose solution (50 μmol/4 mL/kg) was orally administered to the experimental animals of (1), i.e., Group 1 (control group) and Group 2 (diabetes group) 30 minutes after an aqueous glucose solution (450 mg/4 mL/kg) was orally administered. As in (2-1), expired air was collected in each group before the U-$^{13}C$-glucose administration (0 minutes) and at each point in time (10, 20, 30, 40, 50, 60, 80, 100, and 120 minutes) after the U-$^{13}C$-glucose administration. $\Delta^{13}C$(‰) was determined from the concentration of $^{13}CO_2$ excreted in the expired air. FIG. 8 shows the expired air patterns (changes in the $\Delta^{13}C$(‰) in the expired air).
(2-2-3) An aqueous U-$^{13}C$-glucose solution (50 μmol/mL/kg) was intravenously administered to the experimental animals of (1), i.e., Group 1 (control group) and Group 2 (diabetes group) 30 minutes after an aqueous glucose solution (450 mg/4 mL/kg) was orally administered. As in (2-1), expired air was collected in each group before the U-$^{13}C$-glucose administration (0 minutes) and at each point in time (10, 20, 30, 40, 50, 60, 80, 100, and 120 minutes) after the U-$^{13}C$-glucose administration. $\Delta^{13}C$(‰) was determined from the concentration of $^{13}CO_2$ excreted in the expired air. FIG. 9 shows the expired air patterns (changes in the $\Delta^{13}C$(‰) in the expired air).
(2-2-4) An aqueous U-$^{13}C$-glucose solution (50 μmol/mL/kg) was intravenously administered to the experimental animals of (1), i.e., Group 1 (control group) and Group 2 (diabetes group) 30 minutes after an aqueous glucose solution (2 g/4 mL/kg) was orally administered. As in (2-1), expired air was collected in each group before hue U-$^{13}C$-glucose administration (0 minutes) and at each point in time (10, 20, 30, 40, 50, 60, 80, 100, and 120 minutes) after the U-$^{13}C$-glucose administration. $\Delta^{13}C$(‰) was determined from the concentration of $^{13}CO_2$ excreted in the expired air. FIG. 10 shows the expired air patterns (changes in the $\Delta^{13}C$(‰) in the expired air).
(2-2-5) An aqueous U-$^{13}C$-glucose solution (50 μmol/mL/kg) was intravenously administered to the experimental animals of (1), i.e., Group 1 (control group) and Group 2 (diabetes group) 30 minutes after an enteral nutrition agent (protein and amino acid preparation; trade name: "Racol (registered trademark) liquid for Enteral Use," EN Otsuka Pharmaceutical Co., Ltd.) was orally administered in an amount of 4 ml/kg. As in (2-1), expired air was collected in each group before the U-$^{13}C$-glucose administration (0 minutes) and at each point in time (10, 20, 30, 40, 50, 60, 80, 100, and 120 minutes) after the U-$^{13}C$-glucose administration. $\Delta^{13}C$(‰) was determined from the concentration of $^{13}CO_2$ excreted in the expired air. FIG. 11 shows the expired air patterns (changes in the $\Delta^{13}C$(‰) in the expired air).

In each of FIGS. 6 to 11, the $\Delta^{13}$(‰) is plotted on the ordinate, whereas the expired air collection time (minutes) after the U-$^{13}C$-glucose administration is plotted on the abscissa. The symbols -□- and -■- respectively indicate the change in the $\Delta^{13}C$(‰) in the expired air over time measured in Group 1 (control group), and the change in the $\Delta^{13}C$(‰) in the expired air over time measured in Group 2 (diabetes group).
(3) Discussions As shown in FIG. 6, the difference between the $\Delta^{13}C$(‰) value of Group 1 (control group) and the $\Delta^{13}C$(‰) value of Group 2 (diabetes group) was small under fasting conditions. In contrast, as shown in FIGS. 7 to 11, the expired air pattern (change in the $\Delta^{13}C$(‰) in the expired air) of Group 1 (control group) was found to be significantly high compared with the expired air pattern (change in the $\Delta^{13}C$(‰) in the expired air) of Group 2 (diabetes group) under glucose-loaded conditions. Specifically, under fasting conditions, there is a difference in the expired air response (expired air pattern, change in the $\Delta^{13}C$(‰) in the expired air) between the healthy group (control group) and the diabetes group; however, the degree of the difference is small. On the other hand, the difference in the expired air response (expired air pattern, change in the $\Delta^{13}C$(‰) in the expired air) between the healthy group and the diabetes group is increased by measurement under glucose-loaded conditions. This confirms that the diabetes group can be distinguished more easily from the healthy group (control group) by performing the measurement under glucose-loaded conditions.

In addition, as shown in FIG. 7, when the saccharide for use in glucose loading and $^{13}C$-glucose were simultaneously administered, overlapping of the initial (in particular, within 10 minutes after the administration) expired air response of Group 1 (control group) and Group 2 (diabetes group) was observed. However, as shown in FIG. 8, when the saccharide was administered (glucose was loaded) before the administration of $^{13}$C-glucose as a test substance, the overlapping of the initial expired air response was eliminated. Further, as is clear from a comparison of FIG. 8 with FIGS. 9 and 10, the difference in the expired air response between Group 1 (control group) and Group 2 (diabetes group), in particular, the difference in the initial (for example within 10 minutes after the administration) expired air response was further widened by changing the administration rout of $^{13}$C-glucose from oral administration (FIG. 8) to intravenous administration (FIGS. 9 and 10).

As seen from the above, the accuracy of measurement of a diabetes stage can be improved with a breath test using $^{13}$C-glucose under glucose-loaded conditions, preferably a breath test using $^{13}$C-glucose under conditions in which a saccharide is administered beforehand to render a subject in a glucose-loaded state, and more preferably a breath test in which $^{13}$C-glucose is intravenously administered.

Further, as shown in FIG. 11, it is confirmed that even when an enteral solution containing protein, fat, sugars, and various mineral components ("Racol (registered trademark) Liquid for Enteral Use") is used instead of a saccharide (glucose) used in glucose loading, a similar result is obtained. Since there is hitherto a concern about the risk of high blood glucose caused by the oral glucose tolerance test (OGTT) in diabetic patients, it is believed that a food or beverage containing protein, fat, sugars, and various mineral components can be an alternative test meal to a saccharide (glucose) hitherto used in OGTT.

Experimental Example 5

Evaluation of Treatment Effect of a Therapeutic Agent for Diabetes
(1) Experimental Method Three groups of ZDF rats (Group A: healthy group (n=4), Group B: diabetes severe onset group (n=6), and Group C: diabetes moderate onset group (n=6)) were used as experimental animals. In the experiment, these ZDF rats were allowed free access to water and feed (containing saccharide, fat, and protein) (MF: Oriental Yeast Co., Ltd.). More specifically, the following experiment was performed under non-fasting conditions.

Metformin (Wako Pure Chemical Industries, Ltd., which is an active ingredient of biguanide therapeutic agents for diabetes (generic name: Melbin), was orally administered to the rats of these groups in an amount of 300 mg/kg every morning for three days. A U-$^{13}$C-glucose solution prepared by the method described in (1) of Experimental Example 1 was intravenously administered 3 hours after the administration of metformin on day 3.

Expired air was collected in the rats of each group before the U-$^{13}$-glucose administration (0 minutes) and at each point in time (10, 20, 30, 40, 50, 60, 80, 100, and 120 minutes) after the U-$^{13}$C-glucose administration. $\Delta^{13}$(‰) was determined with a mass spectrometer for expired air analysis (ABCA: produced by Sercon) from the concentration of $^{13}CO_2$ excreted in the expired air.

(2) Experimental Results

Figure 12:
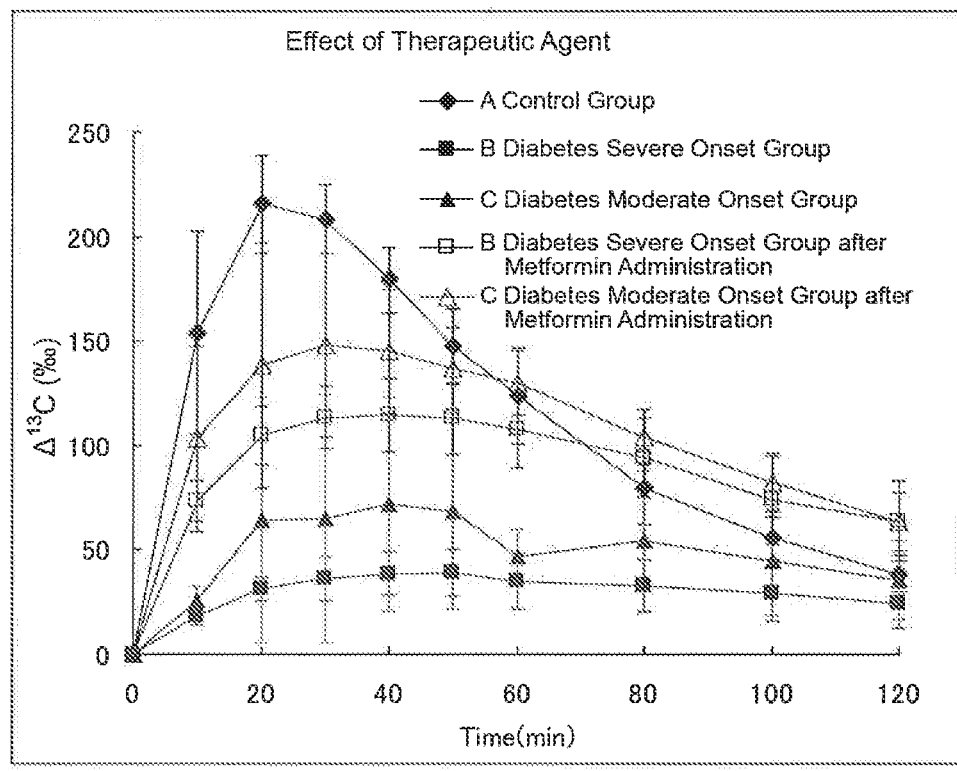
FIG. 12 illustrates the results of Experimental Example 5.

FIG. 12 shows changes in the $\Delta^{13}$C(‰) of the three groups (Group A: healthy group, Group B: diabetes severe onset group, and Group C: diabetes moderate onset group) before the administration of the therapeutic agent for diabetes (no treatment) (Group A: -♦-, Group B: -■-, and Group C: -▲-) and changes in the $\Delta^{13}$C(‰) after the administration of the therapeutic agent for diabetes (Group B: -□- and Group C: -Δ-). In FIG. 12, the $\Delta^{13}$C(‰) is plotted on the ordinate, whereas the expired air collection time (minutes) after the U-$^{13}$C-glucose administration is plotted on the abscissa.

FIG. 12 shows that the expired air patterns (changes in the $\Delta^{13}$C(‰) in the expired air) in both of the two diabetes onset groups (Groups B and C) exhibited higher values by the administration of the therapeutic agent for diabetes, compared with those before the administration of the therapeutic agent for diabetes, and that the glucose metabolism ability was thus enhanced. Specifically, it is revealed that the treatment effect of a therapeutic agent for diabetes can be evaluated with the breath test of the present invention.

This experiment also reveals that the treatment effect of a therapeutic agent for diabetes can be confirmed in a short period of time, i.e., within three days, with a breath test using $^{13}$C-glucose, and in particular a breath test in which $^{13}$C-glucose is intravenously administered (HbA1c measurement obtained about one month after the start of drug treatment is typically used as an index for determination of the treatment effect of a drug).

Experimental Example 6

Evaluation of Treatment Effect after Administration of Insulin

A control group (Wistar rats, male, n=3) and a type 1 diabetes group (STZ rats, male, n=3) were used as experimental animals. In the experiment, these rats were allowed free access to water and feed (containing saccharide, fat, and protein) (MF: Oriental Yeast Co., Ltd.). More specifically, the following experiment was performed under non-fasting conditions.

Rats one week after STZ (streptosocin: SIGMA) were intravenously administered in an amount of 65 mg/mL/kg was used as the type 1 diabetes group (STZ rats).

Insulin (SIGMA) was subcutaneously administered to the type 1 diabetes group in an amount of 30 U/body. A 1-$^{13}$C-glucose solution prepared by the method described in (1) of Experimental Example 1 was intravenously administered to the rats before the administration of insulin, 4 hours after the administration of insulin, or 24 hours after the administration of insulin (however insulin was not administered to the rats of the control group, which is a healthy group). Expired air was collected in the rats of the groups (control group, type 1 diabetes group, insulin-administered 4 h-diabetes group, and insulin-administered 24 h-diabetes group) before the 1-$^{13}$C-glucose administration (0 minutes) and at each point in time (10, 20, 30, 40, 50, 60, 80, 100, and 120 minutes) after the 1-$^{13}$C-glucose administration. $\Delta^{13}$C(‰) was determined with a mass spectrometer for expired air analysis (ABCA: produced by Sercon) from the concentration of $^{13}CO_2$ excreted in the expired air.

Figure 13:
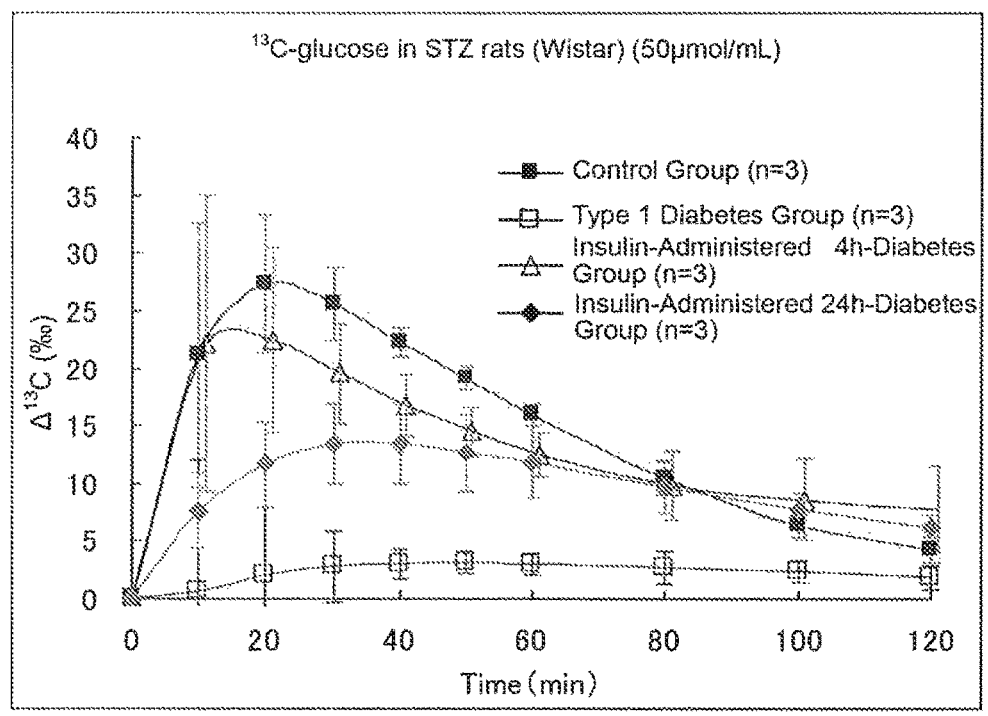
FIG. 13 illustrates the results of Experimental Example 6.

FIG. 13 shows the expired air patterns (changes in the $\Delta^{13}$C(‰)) of the rats of the groups (control group: -■-, type 1 diabetes group: -□-, insulin-administered 4 h-diabetes group: -Δ-, and insulin-administered 24 h-diabetes group: -▲-). In FIG. 13, the $\Delta^{13}$C(‰) is plotted on the ordinate, whereas the expired air collection time (minutes) after the 1-$^{13}$C-glucose administration is plotted on the abscissa. As is clear from the results of the insulin-administered 4 h-diabetes group (-Δ-) in FIG. 13, the $\Delta^{13}$C(‰) while the effect of insulin was sustained was almost the same as that of the control group. As is also clear from the results of the insulin-administered 24 h-diabetes group (-♦-), the expired air pattern (change in the $\Delta^{13}C(‰)$) showed a low value as a result of disappearance of the effect of insulin.

The above experimental results indicate that the breath test using $^{13}C$-glucose of the present invention makes it possible to confirm the effect of insulin on diabetic patients.

The invention claimed is:

1. A method for measuring glucose metabolism of a subject comprising:
    (a) administering a composition to the subject and collecting expired air of the subject after the administration of the composition, wherein the composition comprises glucose labeled with at least one isotope of C; and
    (b) determining a ratio of labeled $CO_2$ amount to unlabeled $CO_2$ amount or a ratio of labeled $CO_2$ amount to total $CO_2$ amount contained in the expired air of step (a) to generate a subject value;
    (c) comparing the subject value, which is "the ratio of labeled $CO_2$ amount to unlabeled $CO_2$ amount or the ratio of labeled $CO_2$ amount to total $CO_2$ amount" obtained in the subject in step (b), to a control value, which is "a ratio of labeled $CO_2$ amount to unlabeled $CO_2$ amount or a ratio of labeled $CO_2$ amount to total $CO_2$ amount" of a non-diabetic subject;
    (d) detecting that the glucose metabolism of the subject is enhanced when the subject value is higher than the control value and (e) determining that the subject whose glucose metabolism is detected to be enhanced in step (d) is in a stage before onset of diabetes.

2. The method according to claim 1, wherein the subject is in a glucose-loaded state.

3. The method according to claim 2, wherein the glucose-loaded subject has taken, before step (a), a saccharide, a food or beverage comprising a saccharide, or a food or beverage comprising a component that is metabolized to a saccharide.

4. The method according to claim 1, wherein the expired air is collected at least at one point in time within 120 minutes after administration of the composition to the subject.

5. The method according to claim 1, wherein the non-diabetic subject is a subject in which diabetes has not developed, and that is not in a stage before onset of diabetes.

6. A method for detecting a stage before onset of diabetes in a subject comprising, using, as an index, glucose metabolism of the subject obtained by a method for measuring glucose metabolism of a subject comprising:
    (a) administering a composition to the subject and collecting expired air of the subject after the administration of the composition, wherein the composition comprises glucose labeled with at least on isotope of C; and
    (b) determining a ratio of labeled $CO_2$ amount to unlabeled $CO_2$ amount or a ratio of labeled $CO_2$ amount to total $CO_2$ amount contained in the expired air of step (a) to generate a subject value; and
    (c) comparing the subject value, which is "the ratio of labeled $CO_2$ amount to unlabeled $CO_2$ amount or the ratio of labeled $CO_2$ amount to total $CO_2$ amount" obtained in the subject in step (b), to a control value, which is "a ratio of labeled $CO_2$ amount to unlabeled $CO_2$ amount or a ratio of labeled $CO_2$ amount to total $CO_2$ amount" of a non-diabetic subject, wherein when the subject value is higher than the control value, the glucose metabolism of the subject is enhanced; and
    determining that the subject is in a stage before onset of diabetes when the glucose metabolism of the subject is enhanced.

7. The method according to claim 6, wherein the non-diabetic subject is a subject in which diabetes has not developed, and that is not in a stage before onset of diabetes.

* * * * *

UNITED STATES PATENT AND TRADEMARK OFFICE
CERTIFICATE OF CORRECTION

PATENT NO. : 10,228,365 B2  
APPLICATION NO. : 14/423021  
DATED : March 12, 2019  
INVENTOR(S) : Makoto Inada et al.

Page 1 of 1

It is certified that error appears in the above-identified patent and that said Letters Patent is hereby corrected as shown below:

In the Claims

Claim 1, Column 29, Line 27, "control value and (e) determining that the subject" should read -- control value and
(e) determining that the subject --.

Claim 1, Column 30, Line 29, "determining that the subject is in a stage before onset of" should read -- (d) determining that the subject is in a stage before onset of --.

Signed and Sealed this  
Sixteenth Day of July, 2019

Andrei Iancu  
*Director of the United States Patent and Trademark Office*